United States Patent [19]

Ushio

[11] Patent Number: 5,673,114
[45] Date of Patent: Sep. 30, 1997

[54] APPARATUS FOR MEASURING OPTICAL ABSORPTION OF SAMPLE AND SAMPLE HOLDER APPLICABLE TO THE SAME

[75] Inventor: Yoshijiro Ushio, Kawasaki, Japan

[73] Assignee: Nikon Corporation, Tokyo, Japan

[21] Appl. No.: 668,862

[22] Filed: Jun. 24, 1996

[51] Int. Cl.$^6$ .................................................. G01N 21/01
[52] U.S. Cl. ............................................. 356/432; 356/440
[58] Field of Search .................................... 356/244, 440, 356/432

[56] References Cited

U.S. PATENT DOCUMENTS 4,943,735  7/1990  Nishikawa .............................. 356/440

OTHER PUBLICATIONS

Rosencwaig et al., "Photoacoustic Measurement of Low-Level Absorptions in Solids" Applied Optics, vol. 20, No. 4, (1981) pp. 606–609 15 Feb. 1981.

Jackson et al., "Piezoelectric Photoacoustic Detection: Theory and Experiment" J. Appl. Phys. vol. 51, No. 6, (1980) pp. 3343–3353 Jun. 1980.

Hutchins, "Mechanisms of Pulsed Photoacoustic Generation", Can. J. Phys., vol. 64, (1986) pp. 1247–1264 (no month).

Tam, "Pulsed–laser Generation of Ultrashort Acoustic Pulses: Application for Thin–film Ultrasonic Measurements", Appl. Phys. Lett. vol. 45, No. 5, (1984) pp. 510–512 1 Sep. 1984.

Rosencwaig et al., "Theory of the Photoacoustic Effect with Solids", J. Appl. Phys., vol. 47, No. 1, (1976) pp. 64–69 Jan. 1976.

Primary Examiner—Richard A. Rosenberger
Attorney, Agent, or Firm—Foley & Lardner

[57] ABSTRACT

A present invention is directed to an apparatus which measures the optical absorption of a sample by photoacoustic measurement and has a configuration for improving the reliability and efficiency in this measurement and is directed to a sample holder applicable to this apparatus. In particular, this sample holder has a specific configuration for improving the reproducibility of acoustic propagation conditions.

36 Claims, 17 Drawing Sheets

TO FREQUENCY SELECTOR

TO FREQUENCY SELECTOR

APPARATUS FOR MEASURING OPTICAL ABSORPTION OF SAMPLE AND SAMPLE HOLDER APPLICABLE TO THE SAME

BACKGROUND OF THE INVENTION

1. Field of the Invention

The present invention relates to an apparatus for measuring the optical absorption of a sample by detecting an acoustic signal corresponding to the optical absorption of the sample. In particular, the present invention relates to a sample holder which is applicable to this apparatus and provided with a configuration which improves the reproducibility of acoustic propagation conditions.

2. Related Background Art

As a variety of applied optical technologies have advanced, demands for optical measurement have become higher. In particular, as a tendency in recent years, greater attention has been paid to physical evaluation of light having a wavelength much longer or shorter than that of visible light. For example, in order to utilize ultra-shortwave light, various excimer lasers or the like have been applied to the fields of minute processing and lithography. Accordingly, it is becoming essential to measure and evaluate optical elements or the like.

Among evaluation items required for physical evaluation of optical elements or the like, one of the most important items is the absorption characteristic with respect to light having a predetermined wavelength.

In order to measure this optical absorption, a method for directly measuring it in an optical manner (system for detecting light intensity by a photosensor) has been used in general. However, there is a limit in this method. Namely, in the case where light from a light source has a short wavelength (200 nm or less), neither light source nor optical quantity measuring technique has been stably established therefor at present. In particular, when it is necessary to measure a minute amount of absorption (minute difference in light intensity), the stability in optical absorption measurement remarkably decreases.

Also, when a pulse laser such as excimer laser is used, upon detection thereof, a problem may occur due to a slow response speed of a photosensor. Further, it is difficult for an optical method to separately measure an amount of optical absorption alone, since it is always detected as a value including an amount of scattering on a surface of a sample or the like.

Accordingly, there have been proposed some methods for measuring a minute amount of optical absorption, replacing the conventional optical techniques. Most of such methods are of type in which optical absorption of a sample is measured as a heat which is a radiationless transition.

A typical method thereof has been known as calorimetry. This method directly measures an increase in temperature due to optical absorption of the sample by a temperature measuring means such as a thermocouple.

Also, there has been another measuring method known as photoacoustic measurement which detects an acoustic signal generated upon a deformation occurring in the sample or an atmosphere in the vicinity thereof due to an increase in temperature or a relaxation (of the deformation) and, backward from thus detected signal, calculates the amount of optical absorption.

Further, recently, there has often been used a method which detects a refractive index distribution or displacement in the sample or in the vicinity thereof occurring due to absorption heating by means of light (by detecting deflection of a beam, light path difference, or the like).

Among these methods, the photoacoustic measurement which performs acoustic measurement has been widely used for measuring the optical absorption of liquids, powders, thin film materials, or the like.

In this method, on the sample or in the atmosphere in the vicinity thereof, a sound corresponding to a change in volume generated upon heating and cooling due to irradiation of intermittent light is detected as being converted into an electric signal by means of a microphone or a transducer made of a piezoelectric element.

When the intensity, phase, or the like of such an electric signal is analyzed, various kinds of information concerning the radiationless transition of the material can be obtained. Since the magnitude of an acoustic wave is in proportion to thermal energy (i.e., amount of optical absorption), the amount of optical absorption can be computed therefrom. (For a detailed theory, see J. Appl. Phys., vol. 47, No. 1, p. 64; J. Appl. Phys., vol. 51, No. 6, p. 3343; and Can. J. Phys., vol. 64, p. 147, for example.)

While the photoacoustic measurement is performed as an analysis method for analyzing the radiationless transition process of a material or the like, it has also been remarked as the above-mentioned optical absorption amount measuring method.

SUMMARY OF THE INVENTION

The object of the present invention is to provide an optical absorption measuring apparatus which performs photoacoustic measurement and improves both reliability and efficiency in measurement as well as a sample holder for the optical absorption measuring apparatus with a configuration which improves the reproducibility of acoustic propagation conditions. In particular, this sample holder has a configuration such that acoustic contact condition of an object to be measured (sample) and the holder body with each other can be held constantly in the optical absorption measuring apparatus. According to this measuring method, even in the case where optical absorption is minute, the amount of detected signal can be increased when a high light intensity is used, thereby enabling measurement with a high sensitivity.

After having studied the prior art in order to obtain the above-mentioned apparatus and sample holder, the inventors have found the following problems to be overcome.

Namely, one of the most important points to be considered when measuring an amount of optical absorption of a sample by photoacoustic measurement is the dependency of the signal intensity upon the acoustic wave propagation condition.

Since the intensity of an acoustic wave changes due to the acoustic wave propagation condition in the space from the place of absorption to an acoustic sensor, even when light irradiating conditions for a sample are the same, it may differ according to the distance between the sample (and a sound generating source which is a portion to be irradiated with light) and the acoustic sensor and an acoustic junction condition therebetween. Accordingly, careful attention is needed when signal intensities among different samples are compared with each other.

In remote measurement by means of a microphone, it is relatively easy to attain the reproducibility in acoustic propagation from a sample, whereby the signal can be easily standardized. Also, in the measurement of a liquid sample or a gas sample, the reproducibility in signal intensity can be attained when the settings of a cell containing the sample, the light source light (measurement light), and the acoustic sensor are constantly held.

However, when acoustic detection of contact type with a high signal intensity is to be performed in measurement of a solid sample such as a thin film sample prepared on a glass substrate, it is not easy to hold the acoustic propagation condition thereof constantly.

Here, of particular importance is the contact condition of the contacting portions of the solid sample and the acoustic sensor or sample holder with each other. When the acoustic propagation condition (i.e., contact condition) in the contacting portions changes when samples are exchanged, the signal intensity also changes.

For example, when a solid sample and a sample holder (or an acoustic sensor) are brought into contact with each other as being directly pressed against each other, a slight gap layer is formed therebetween due to irregularities (or dirt) on their surfaces since they are rigid solids in general.

The inventors have confirmed it therefore difficult to hold the acoustic contact condition constantly and that the signal intensity is likely to shift (fluctuate) greatly, thereby deteriorating the reliability in measurement.

Also, in the case where their contact is attained by means of grease or the like which is often used as acoustic matching material, unless their pressing operation is carefully effected, the thickness in this matching material layer or the condition of its contact with the sample is likely to change so as to shift (fluctuate) the acoustic intensity greatly, thereby deteriorating the reliability in measurement.

Further, when grease or the like is used, since it adheres to the sample and the holder when the sample is set, it is necessary to wash the sample and the holder and apply or supply the matching material thereto each time the samples are exchanged, whereby the efficiency in measurement decreases.

Accordingly, there has been proposed a method in which a sample is disposed in a liquid and a sound propagated through the liquid is measured (see Appl. Opt., vol. 20, No. 4, p. 606).

However, in this method, in terms of its disposition, since the sample is totally submerged in the liquid, the measurement light passes through the liquid. As a result, the measurement becomes very difficult unless the liquid can transmit substantially the whole measurement light therethrough.

In particular, this method is not practical when light having a wavelength in ultraviolet region is used for measurement, since there rarely exist liquids which can transmit substantially the whole measurement light therethrough. Also, even when there exists a liquid which can transmit substantially the whole measurement light therethrough, it is necessary to consider optical characteristics (absorption, reflection, scattering, and the like) of this liquid, thereby complicating the evaluation of the detected value, together with a possible deterioration of accuracy.

In order to overcome the foregoing circumstances, the apparatus in accordance with the present invention measures an acoustic signal generated upon a change in volume of a sample due to optical absorption of the sample irradiated with measurement light having a predetermined wavelength, thereby measuring the optical absorption of the sample with a favorable reproducibility. For example, as shown in FIGS. 1 and 2, a specific configuration of this apparatus comprises, at least, a housing 2 for providing a dark room and a sample holder (holder body 7) which is disposed within the housing and applicable to an apparatus for measuring optical absorption of a sample 90 with respect to measurement light having a predetermined wavelength emitted from a light source 1 by utilizing a photoacoustic measuring method. In a preferable embodiment, this apparatus comprises, as an intensity control system for the measurement light, an optical system 4 which is disposed within the housing 2 and placed in a light path of the measurement light traveling toward the sample 90 and an optical monitor (a light intensity monitor including a photosensor such as a photomultiplier, or the like) 11 which is disposed within the housing 2 and is used for receiving a part (e.g., a luminous flux separated by a luminous-flux separator 5 such as a half mirror) of the measurement light.

In particular, as shown in FIG. 3, for example, the above-mentioned sample holder comprises the holder body 7 having a sample supporting section 77 which saves a predetermined amount of a liquid 32 and supports a measurement sample 9 to be measured (including the sample 90 such as a thin film, which is an object to be measured, and a sample body 91 such as a glass material which supports the sample 90) while immersing a part of the sample 90 in the liquid 32. This sample supporting section 77 includes a depression 75 defined by individual members constituting the holder body 7 and an opening 76 through which a portion 33 of the sample 90 is placed above the a liquid level 32a of the liquid 32. Further, the above-mentioned sample holder comprises an acoustic sensor 8 for detecting an acoustic signal generated upon a change in volume of the sample 90 due to optical absorption of the sample 90 when irradiated with the measurement light and a holding mechanism for directly attaching the acoustic sensor 8 to a predetermined position of the holder body 7. This holding mechanism may include an adhesive 31 shown in FIG. 3 or a through hole 34 (formed in a member 72 constituting the holder body 7) shown in FIG. 4 and the adhesive 31.

The holding mechanism shown in FIG. 3 fixes the acoustic sensor 8 to a predetermined position of the holder body 7 while the holder body 7 and the acoustic sensor 8 are acoustically matched with each other. Also, the holding mechanism shown in FIG. 4 fixes the acoustic sensor 8 to a predetermined position of the holder body 7 while the liquid 32 and the acoustic sensor 8 are acoustically matched with each other. Here, in order to enable precise measurement of optical absorption, the holder body 7 is made of a material whose loss corresponding to its absorption and scattering is not greater than 0.1% with respect to the measurement light having a predetermined wavelength. More preferably, an anti-reflection coating 701 is disposed on the surface of the holder body 7 (see FIGS. 6 to 8).

The holder body 7 further comprises a positioning mechanism for defining the position of the measurement sample 9. In a first embodiment of the positioning mechanism, as shown in FIG. 6, the sample supporting section 77 of the holder body 7 has surfaces 73a and 72a for defining a position to which the measurement sample 9 is fixed. In this case, the sample supporting section 77 of the holder body 7 has a maximum depth D which by which the portion of the sample 90 supported by the sample body 91 to be irradiated with the measurement light (including at least the portion 33 to be irradiated with the measurement light) is sufficiently placed above the liquid level 32a of the liquid 32 by way of the opening 76 of the sample supporting section 77.

Also, in a second embodiment of the positioning mechanism, as shown in FIG. 7, the measurement sample 9 is pressed against the surface 72a of a member 72 constituting the holder body 7. In this case, the surface 72a of the member 72 functions to define a position to which the measurement sample 9 is fixed.

Further, as shown in FIG. 8, there is a third embodiment of the positioning mechanism, in which members constituting the holder body 7 are respectively provided with taper surfaces 71b, 72b, and 73b such that the holder body 7 as a whole is inclined by a predetermined angle $\theta_2$ with respect to a plane P1 which is in parallel to irradiating direction L3 of the measurement light. In this case, a surface 71a of the member 71 and a surface 73c of the member 73 function to define a position to which the measurement sample 9 is fixed.

Preferably, the above-mentioned sample holder further comprises the following configuration. Namely, as shown in FIG. 16, the holder body 7 comprises a liquid level adjusting mechanism for constantly holding the liquid level 32a of the liquid 32 such that a part of the measurement sample 9 is immersed therein and liquid containers 700a and 700b which are disposed at predetermined positions of the holder body 7 and accommodate, of the liquid retained in the depression 75 of the sample supporting section 77, an unnecessary liquid 32b guided by the liquid level adjusting mechanism.

As shown in FIGS. 16 and 17, for example, a first embodiment of the above-mentioned liquid level adjusting mechanism is realized by the opening 76 of the depression 75 included in the sample supporting section 77. As shown in FIG. 20, for example, a second embodiment of the liquid level adjusting mechanism comprises a guiding section 300 which is provided at a predetermined position of a member 71A constituting the sample holder 7 and used for guiding the unnecessary liquid 32b to a liquid container 700c. This guiding section 300 guides, of the liquid 32 retained in the depression 75, the unnecessary liquid 32b to the liquid container 700c such that its reference surface 300a coincides with the liquid level 32a.

The apparatus in accordance with the present invention further comprises a liquid amount adjusting system for constantly holding the liquid level 32a of the liquid 32 to be saved in the depression 75 of the sample supporting section 77 of the holder body 7. Here, the above-mentioned liquid level adjusting mechanism provided with the sample holder 7 is included in this liquid amount adjusting system.

This liquid amount adjusting system includes a liquid supplying mechanism for supplying the liquid 32 to the sample supporting section 77 of the holder body 7. This liquid supplying mechanism may be realized by an injector 50 shown in FIG. 16 or the like. Alternatively, as shown in FIG. 21, it may be configured so as to continuously supply a predetermined amount in a predetermined time.

This liquid amount adjusting system further includes a liquid recovering mechanism for removing a part (unnecessary liquid 32b) of the liquid 32 retained in the depression 75 of the sample supporting section 77 of the holder body 7. As shown in FIG. 20, this liquid recovering mechanism may be realized by an injector 520. Alternatively, as shown in FIG. 22, it may be configured such that the unnecessary liquid 32b is collected by means of a pump 580 or the like.

Preferably, as shown in FIGS. 21 and 22, in order to constantly hold the liquid temperature so as to further improve the reproducibility in measurement of optical absorption, the apparatus further comprises a liquid temperature control system 400 for controlling the temperature of the liquid 32 supplied to the depression 75 of the sample supporting section 77 of the holder body 7.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

In the following, the optical absorption measuring apparatus in accordance with the present invention and sample holders applicable to this apparatus will be explained with reference to FIGS. 1 to 22.

The optical absorption measuring apparatus in accordance with the present invention is a system in which light from a light source is converged by various kinds of optical systems and then a sample is irradiated with thus converged light. When irradiating the sample with the light, the apparatus changes the light intensity (irradiation light intensity) by means of an appropriate light intensity adjusting section, monitors this light intensity, and calculates the amount of optical absorption based on a correlation between the irradiation light intensity and an acoustic signal.

Figure 1:
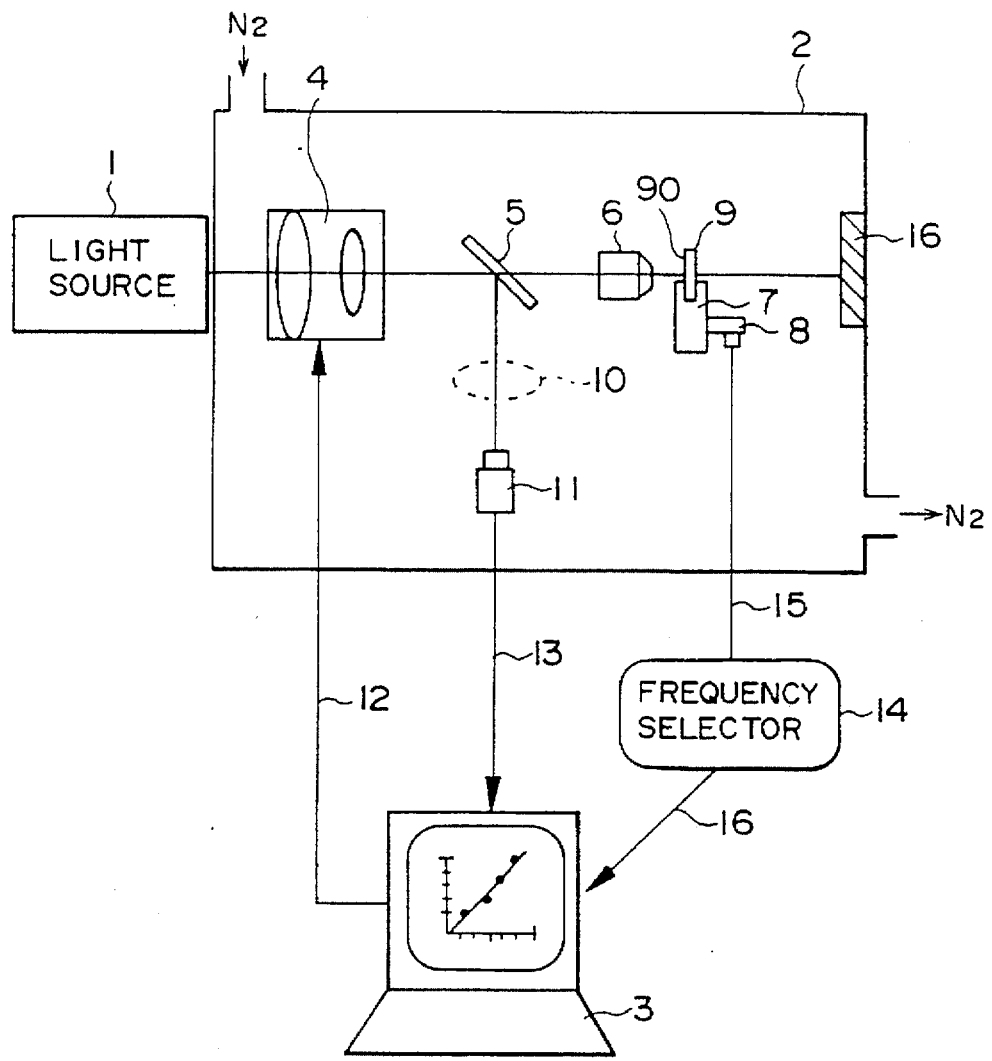
FIG. 1 is a view showing a schematic configuration of an optical absorption measuring apparatus in accordance with the present invention.

In particular, as shown in FIG. 1, this apparatus comprises a housing 2 for defining a dark room purged with nitrogen. A measurement sample 9 (held by a holder body 7) is disposed at a predetermined position within the housing 2, thereby the optical absorption of a sample 90 is measured in a nitrogen atmosphere. Measurement light with a predetermined wavelength is supplied from a light source 1 disposed outside of the housing 2. The measurement light emitted into the nitrogen atmosphere is guided, by way of an optical system 4 constituted by a plurality of lenses, to a luminous-flux separator 5 such as a half mirror. This luminous-flux separator 5 guides a part of the measurement light to an optical monitor (a light intensity monitor including a photosensor such as a photomultiplier, or the like) 11 for receiving the measurement light, while guiding the rest of the measurement light to the sample 90 by way of an objective lens 6. An electric signal 13 (containing information of light intensity of the measurement light) from the light intensity monitor 11 is input into a computer 3, whereas a control signal 12 for adjusting the light intensity of measurement light is output from the computer 3. The light intensity monitor 11, computer 3, and optical system 4 constitute an intensity adjusting system for the measurement light. Here, a converging lens system 10 may be disposed in a branched light path between the luminous-flux separator 5 and the light intensity monitor 11.

Figure 2:
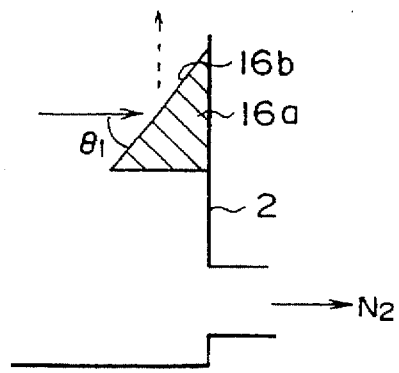
FIG. 2 is a view showing another configuration of an absorber 16 (measurement light absorbing block) shown in FIG. 1.

On the other hand, the measurement light guided to the sample by way of the luminous-flux separator 5 and the objective lens 6 is absorbed by an absorber 16. As another configuration of this absorber 16, for example, as shown in FIG. 2, an absorber 16a having a surface 16b inclined by a predetermined angle $\theta_1$ with respect to the advancing direction of the measurement light may be disposed at an inner wall of the housing 2. In this case, even when a part of the measurement light is accidentally reflected by the surface 16b of the absorber 16a, the reflected light is prevented from returning to the measurement sample 9 again.

An acoustic signal resulting from the optical absorption of the sample 90 is detected by an acoustic sensor 8 by way of the liquid 32 and the holder body 7. Thus detected signal 15 is appropriately filtered by a frequency selector 14 (having a signal amplifying function), whereby a desired acoustic signal 16 thus amplified is input into the computer 3. The computer 3 calculates the amount of optical absorption of the sample 90 on the basis of the light intensity signal 13 from the light intensity monitor 11 and the acoustic signal 16 from the acoustic sensor 8.

Here, the sample 90 includes a thin film sample or the like held on a surface of a glass plate or the like which is a sample body 91. Also, in this specification, the sample 90, which is an object to be measured, and the sample body 91 such as a glass substrate, which supports the sample 90, are collectively referred to as the measurement sample 9.

Figure 3:
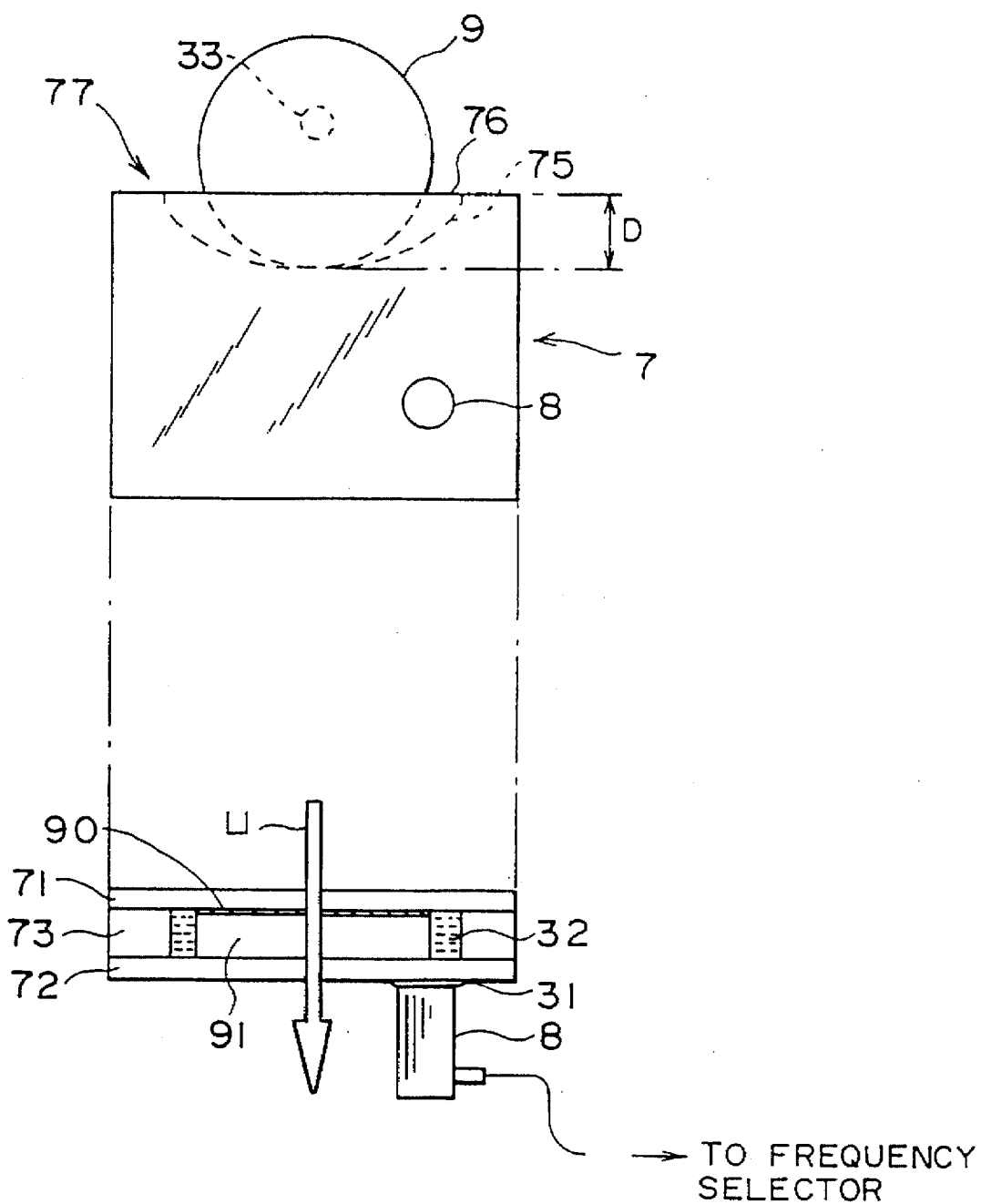
FIG. 3 is a view showing a configuration of a first embodiment of the sample holder in accordance with the present invention.

FIG. 3 is a view showing a configuration of a first embodiment of the sample holder in accordance with the present invention. The measurement sample 9 shown in this drawing comprises, as mentioned above, the glass substrate 91 (sample body) and the solid sample 90 which is a thin film formed on the glass substrate 91. The substrate 91 is made of a predetermined material with a predetermined size, while having a sufficiently smooth substrate surface. Preferably, the amount of measurement light absorbed by the substrate 91 is sufficiently smaller than the amount of measurement light absorbed by the thin film 90 to be measured. In this embodiment, the glass substrate is formed like a circular pellet.

Here, a sample supporting section 77 includes a depression 75 defined by members 71, 72, and 73 (formed with an arc-like groove) constituting the holder body 7 and an opening 76. A liquid 32 has been injected into the depression 75 such that a space between the measurement sample 9 and the surface of the holder body defining the depression 75 is filled therewith.

As the liquid 32, a liquid having such a specific gravity that the measurement sample 9 does not rise to the surface thereof is used. Also, of the measurement sample 9, a portion (spot 33) which is not immersed in the liquid 32 is irradiated with the measurement light. Here, arrow L1 indicates the incident direction of the measurement light.

In this embodiment, as viewing in the incident direction of the measurement light, the thickness of the measurement sample 9 and the width of the depression 75 have substantially the same size. Accordingly, in the depression 75, the measurement sample 9 is fixed in the direction of L1 so as to be always placed at a predetermined position. Also, maximum depth D of the depression 75 is such that the spot 33 is sufficiently placed above the opening 76 (coinciding with a liquid level).

Since the sample holder for the optical absorption measuring apparatus in accordance with the present invention is configured such that the space between the measurement sample 9 and the holder body 7 is filled with the liquid 32, there occurs no air gap which becomes problematic in general when solids are attached to each other by contact pressure. Also, according to this configuration, acoustic impedance matching becomes favorable, thereby improving the reproducibility of the acoustic propagation condition while increasing the intensity of the detected signal. Here, in this embodiment, the acoustic sensor 8 (sound probing device) is directly bonded and fixed to the member 72 constituting the holder body 7 by means of an adhesive 31 (included in holding mechanism).

Namely, the sample holder for the optical absorption measuring apparatus in accordance with the present invention can constantly hold the acoustic contact condition of the solid sample 90 and the acoustic sensor 8 with respect to each other in a simple manner. As a result, it can improve the reliability and efficiency in the measurement of optical absorption.

Here, in the method mentioned above as a technique for performing acoustic measurement in which the sample is disposed in the liquid (see Appl. Opt., vol. 20, No. 4, p. 606), the sample as a whole must be immersed in the liquid in terms of its configuration. Accordingly, the measurement light inevitably passes through the liquid, whereby the measurement becomes very difficult unless the liquid can transmit substantially the whole measurement light therethrough.

In particular, this method is not practical when light having a wavelength in ultraviolet region is used for measurement, since there rarely exist liquids which can transmit substantially the whole measurement light therethrough. Also, even when there exists a liquid which can transmit substantially the whole measurement light therethrough, it is necessary to take account of optical characteristics (absorption, reflection, scattering, and the like) of this liquid. Accordingly, evaluation of the detected value becomes complicated, while there is a possibility that accuracy is deteriorated.

On the contrary, the sample holder of the present invention is configured (arranged) such that the measurement light does not pass through the holder body 7 and the liquid 32. Accordingly, the optical absorption measurement using the sample holder of the present invention has a great advantage in that it is not necessary to particularly take account of restrictions caused by the optical characteristics of the liquid 32 and constituents of the holder body 7 with respect to the measurement light.

Though there has also been known a method in which a liquid such as water is inserted between the acoustic sensor 8 and the measurement sample 9, as a thin layer, so as to attain matching (Appl. Phys. Lett., vol. 45, No. 5, p. 510, etc), in this method, setting is quite troublesome, while it is necessary to take care of surplus liquid after the setting.

By contrast, the optical absorption measurement using the sample holder of the present invention has a great advantage in that the setting is easily completed when the measurement sample 9 is simply inserted into a predetermined amount of the liquid 32.

The detection of the acoustic signal in accordance with the present invention is effected by a piezoelectric element (an example of the acoustic sensor 8) which is directly attached to the holder body 7 by means of the adhesive 31 (included in holding mechanism) as mentioned above.

This piezoelectric element 8 is firmly fixed to the holder body 7. Accordingly, acoustic matching is stably attained between the piezoelectric element 8 and the holder body 7 (member 72), thereby improving the reliability in the optical absorption measurement.

Figure 4:
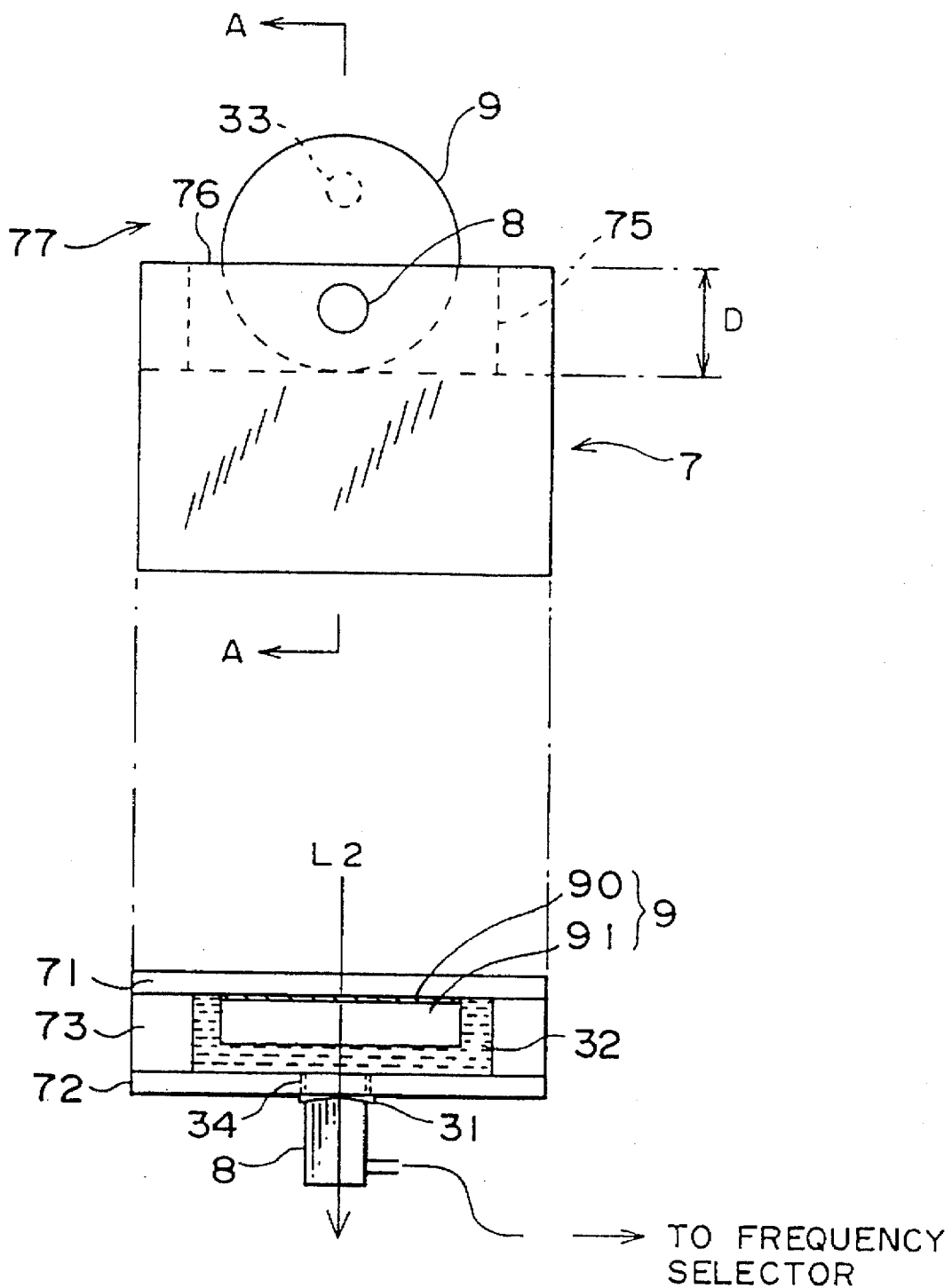
FIG. 4 is a view showing a configuration of a first application of the sample holder shown in FIG. 3, the first application having a holding mechanism different from that of the sample holder shown in FIG. 3.

Here, the holding mechanism for attaching the acoustic sensor 8 to the holder body 7 may be configured as shown in FIG. 4, for example. Namely, the acoustic sensor 8 may be fixed to the holder body 72 by means of the adhesive 31 while a part of the acoustic sensor 8 is inserted into a through hole 34 formed in the member 72. According to this configuration, acoustic matching between the liquid 32 and the acoustic sensor 8 can be attained, thereby improving the reliability of the optical absorption measurement. In this drawing, L2 indicates the incident direction of the measurement light.

Preferably, in order to maintain the reproducibility of sound, the amount of the liquid 32 filled in the depression 75 of the sample supporting section 77 of the holder body 7 is made constant. Accordingly, for example, before the measurement sample 9 is set into the depression 75 of the sample supporting section 77 of the holder body 7, a predetermined amount of the liquid 32 is introduced into the depression 75 of the sample supporting section 77 of the holder body 7. Alternatively, after the measurement sample 9 is set into the depression 75 of the sample supporting section 77, a predetermined amount of the liquid 32 may be injected into the depression 75 such that the gap between the measurement sample 9 and the holder body 7 is filled with the liquid 32.

In any case, when a marking for monitoring the liquid amount is effected in the inner wall of the depression 75, the optical absorption can be measured with a constant liquid amount.

Also, in order to maintain the reproducibility of sound, it is preferable to provide a liquid amount adjusting system for adjusting the amount of the liquid 32 filled in the depression 75 of the sample supporting section 77 to a constant or substantially constant value (for constantly holding a liquid level 32a). This system may be united with or separated from the holder body 7.

This liquid amount adjusting system further includes a liquid supplying mechanism for filling the liquid 32 into the depression 75, a liquid recovering mechanism for removing the liquid 32 or unnecessary part thereof from the depression 75, or both of these mechanisms.

Since the liquid amount within the depression 75 decreases, though slightly, when the measurement sample 9 is exchanged for another one, for example; it is preferably supplemented when appropriate. Accordingly, in the case where an injector needle type member 50 (an example of the liquid supplying mechanism for filling the liquid 32 into the depression 75, the liquid recovering mechanism for removing the liquid 32 from the depression 75, or both of these mechanisms) such as that shown in FIG. 5 is used, when the liquid 32 is supplemented from the gap between the measurement sample 9 and the inner wall of the depression 75, the liquid 32 can be supplemented (or filled in) even under the condition where the measurement sample 9 is set in the sample supporting section 77.

The above-mentioned injector needle type member 50 is preferable in that it can minutely control the amount of liquid to be injected while functioning to eliminate the excess liquid.

When the liquid 32 is supplemented in excess, it may be removed from the depression 75 by means of the above-mentioned member 50 or the like. Also, a valve for allowing the liquid 32 to escape therefrom (which is an example of the liquid recovering mechanism for removing the liquid 32 from the depression 75 while functioning as the liquid level adjusting mechanism) may be provided so as to remove the liquid 32 from the depression 75.

Figure 5:
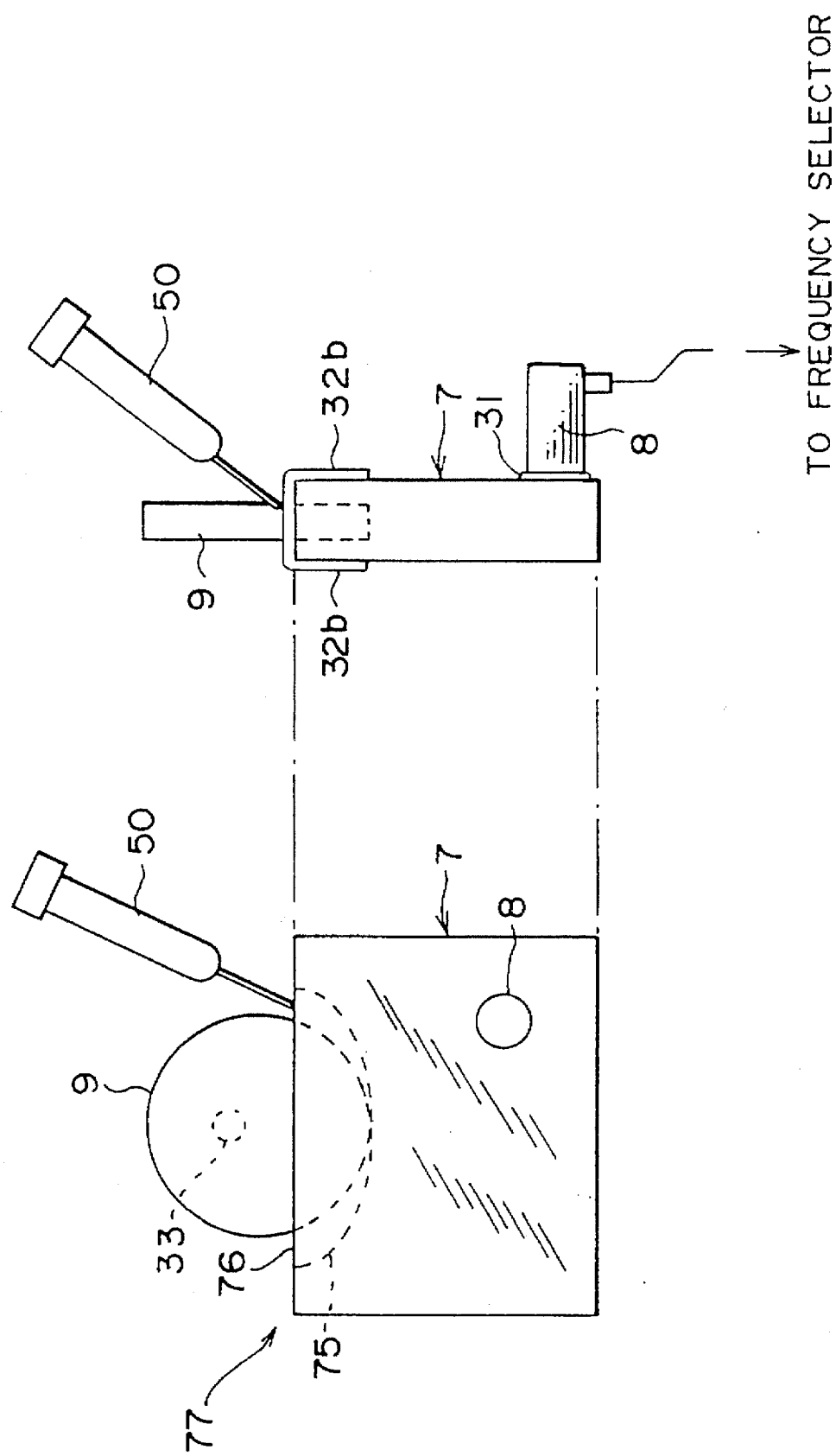
FIG. 5 is a view showing a first embodiment of a liquid supplying mechanism of a liquid amount adjusting system.

Alternatively, as shown in FIG. 5, a configuration by which the excess liquid 32b injected (filled) into the depression 75 flows out through the opening 76 of the sample supporting section 77 may be used. This configuration (an example of the liquid recovering mechanism for removing the liquid 32 from the depression 75) is easy to utilize since it is simple. This opening 76 also functions as a liquid level adjusting mechanism.

In the sample holder of this configuration, even when the liquid flows out, it does not influence the measuring portion 33 of the measurement sample 9. Also, the inventors have confirmed that, even when the liquid 32b thus flowed out adheres to the outer wall of the measurement sample 9, the acoustic signal is not influenced thereby.

In the optical absorption measurement in accordance with the present invention, it is necessary to take account of the characteristics of the liquid 32 filling the depression 75. For example, when a liquid having a high viscosity is used, bubbles may occur in the liquid. These bubbles may greatly influence the acoustic propagation. Accordingly, the liquid filling the depression 75 preferably does not contain any bubbles.

The inventors have confirmed that, even in the case where water is used, the reproducibility of signal intensity cannot be attained when there exist bubbles. Accordingly, a liquid with a low viscosity within which bubbles are unlikely to occur is preferably used since it eliminates the trouble of removing the bubbles.

Also, it is necessary to take account of the case where the liquid 32 within the depression 75 evaporates during the measurement of the optical absorption of the measurement sample 9 such that the liquid amount remarkably changes. Actually, when the measurement is effected with methyl alcohol under a nitrogen atmosphere (where moisture is nearly 0%), a remarkable change in signal is recognized in about 15 minutes due to the evaporation of the liquid. In order to perform a long-time measurement, it is necessary to use a liquid which evaporates as little as possible or to provide an additional liquid supplying mechanism.

Further, in order to facilitate the measurement of optical absorption of the measurement sample 9, it is preferable to use a liquid which can be easily removed when attached to the measurement sample 9.

One of the most important items to be considered when conducting a measurement for optical absorption is the influence of noise upon the measurement. In order to effect the photoacoustic measurement with a higher accuracy, it is necessary to take notice, in particular, that the scattered light component of the light (measurement light) incident on the measurement sample 9 and the stray light from the optical system disposed in the light path of the measurement light do not influence the measurement.

The influences of these undesirable scattered light and stray light upon the measurement can be suppressed to a certain extent when the disposition of the above-mentioned optical system or the like is contrived well or the time period for detecting the acoustic signal is selected. However, in order to eliminate the influence occurring due to the above-mentioned scattered light or stray light absorbed by the holder body 7, it is preferable for the holder body 7 to be constituted by a material which absorbs the measurement light as little as possible, i.e., a material which transmits or reflects the measurement light.

Accordingly, it is preferable to use a material whose loss corresponding to its absorption and scattering with respect to the measurement light is 0.1% or less as the members 71, 72, and 73 constituting the holder body 7.

Figure 6:
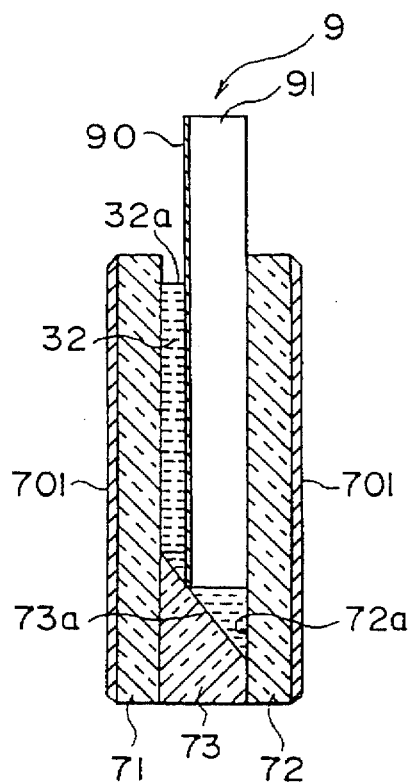
FIG. 6 is a view showing a first embodiment of a positioning mechanism in the sample holder in accordance with the present invention.
Figure 7:
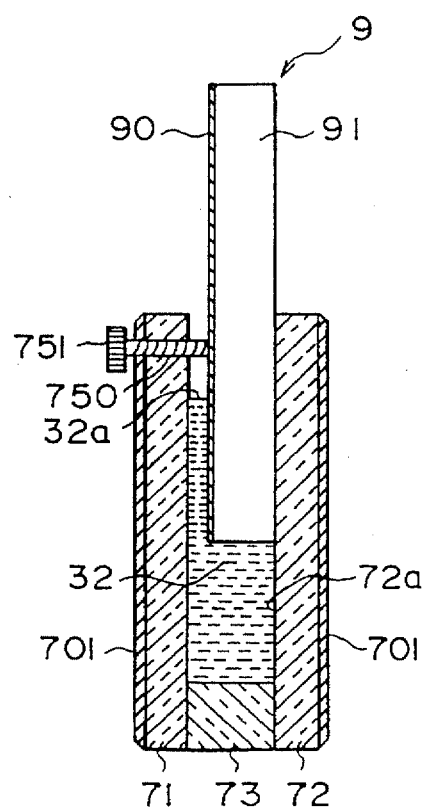
FIG. 7 is a view showing a second embodiment of a positioning mechanism in the sample holder in accordance with the present invention.
Figure 8:
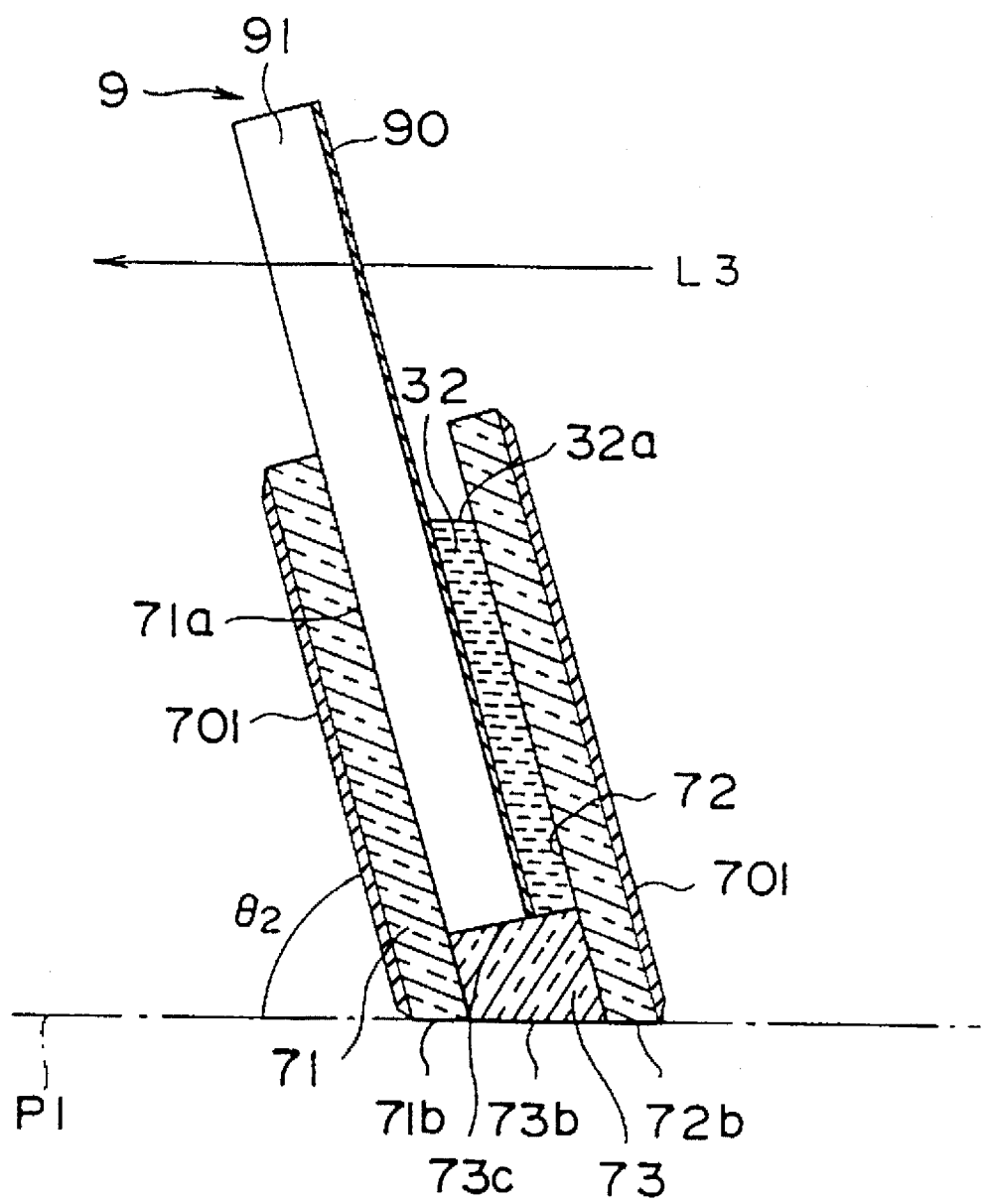
FIG. 8 is a view showing a third embodiment of a positioning mechanism in the sample holder in accordance with the present invention.

Also, the members 71, 72, and 73 constituting the holder body 7 are preferably subjected to a treatment by which the measurement light is prevented from being reflected thereon. Accordingly, the holder body 7 shown in FIGS. 6 to 8 is provided with an anti-reflection coating which is constituted by thin films laminated on the surface of each of the members 71 and 72, for example.

The material of the holder body 7 (e.g., material for the members 71, 72, and 73) preferably has an acoustic impedance ($N.s.m^{-3}$) such as that of aluminum. Such a material having a high acoustic impedance is preferably used since it attenuates the acoustic signal propagated therethrough less than the air or liquid does.

In addition to the above-mentioned aluminum (with an acoustic impedance of $8.2 \times 10^6$ $N.s.m^{-3}$), examples of the material for constituting the holder body 7 include glass material (with an acoustic impedance of $6.35 \times 10^6$ $N.s.m^{-3}$). Also, a rubber material has an acoustic impedance of $0.12 \times 10^6$ $N.s.m^{-3}$ which is much lower than that of the above-mentioned materials. Such a rubber material is suitable for a structure blocking the propagation of the acoustic signal.

Further, the acoustic impedance of liquids will be discussed. For example, water has an acoustic impedance of $1.5 \times 10^6$ $N.s.m^{-3}$, while other liquids similarly have an acoustic impedance within the range of $1.0 \times 10^6$ to $1.5 \times 10^6$ $N.s.m^{-3}$. The acoustic impedance of these liquids is much greater than that of the air, i.e., 430 $N.s.m^{-3}$.

Accordingly, a liquid which has a viscosity much lower than that of grease while having an acoustic impedance much greater than the air is preferably used as the liquid applicable to the present invention.

In order to attain a better reproducibility in the optical absorption measurement, it is preferable to constantly hold the position at which the measurement sample 9 held by the sample supporting section 77 is disposed. Accordingly, the sample holder is preferably provided with a positioning mechanism for the measurement sample 9. For example, in the positioning mechanism of FIG. 3, the position of the measurement sample 9 in a direction perpendicular to the incident angle L1 of the measurement light is defined as being supported by a curved surface of the bottom portion of the depression 75 in contact therewith. Also, the position of the measurement sample 9 in the incident direction L1 of the measurement light is defined when the width of the depression 75 is made to coincide with the thickness of the measurement sample 9. Thus, the positioning mechanism of FIG. 3 holds the measurement sample 9 at a predetermined position.

Also, as shown in FIG. 6, a taper surface 73a functioning as a guide may be formed on the bottom surface of the depression 75 so as to position the measurement sample 9 in its thickness direction (corresponding to the incident direction of the measurement light). Here, in this positioning mechanism, the surfaces 73a and 72a function to define the position at which the measurement sample 9 is disposed.

Alternatively, as shown in FIG. 7, a mechanism may fix the measurement sample 9 by pressure. In such a mechanism, a screw or spring is used in general. Preferably, a screw (an example of the sample positioning mechanism) 751 (engaging with a thread groove 750 formed in the member 71) for pressing the measurement sample 9 is not disposed on the light path of the measurement light, while always pressing the measurement sample 9 at the same position. The positioning mechanism shown in FIG. 7 is constituted by the screw 750 and the surface 72a.

Further, as shown in FIG. 8, the holder body 7, as a whole, may be inclined by a predetermined angle $\eta_2$ with respect to incident direction L3 of the measurement light. In this configuration, the measurement sample 9, due to the weight thereof, naturally comes into contact with one wall 71a of the depression 75, thereby realizing a state in which the measurement sample 9 is disposed at a predetermined position. Also, in this case, when there is a demand for making the light vertically incident on the measurement sample 9, the light path of the measurement light is bent by an appropriate means such as mirror such that the measurement light is vertically incident on the measurement sample 9. Here, the angle of inclination of the holder body 7 is defined by surfaces 71b, 72b, and 73b. Also, in this positioning mechanism, surfaces 71a and 73c function to define the position at which the measurement sample 9 is disposed.

Here, FIGS. 6 to 8 are cross-sectional views of the holder body along line A—A in FIG. 4, in which the acoustic sensor 8 is not depicted for the convenience of explanation.

EXPERIMENT 1

In the following, the result of the photoacoustic measurement performed with an optical absorption measuring apparatus (FIG. 1) to which the sample holder shown in FIG. 3 was applied will be explained.

The light source 1 is an ArF excimer laser (with a wavelength of 193 nm) whose pulse width is about 20 nsec. The pulse measurement light is converged by the lens optical system 4 so as to irradiate the measurement sample 9 disposed at the sample supporting section 77 of the holder body 7 which is placed at a predetermined position within the housing 2. The diameter of the measurement light on the sample surface is about 3 mm.

The intensity of the measurement light is adjusted by a zoom lens inserted into the optical system 4. Also, as depicted, the intensity of the measurement light is monitored by the light intensity monitor 11 (bi-planar type photomultiplier) which is disposed at a branch light path (in which the lens system 10 may be disposed) formed due to the reflection effected by quartz glass (luminous-flux separator 5).

The light transmitted through the measurement sample 9 is cut off by the absorber 16 (or the absorber 16a shown in FIG. 21) such that it is prevented from returning to the measurement sample 9. Here, the absorber is preferably constituted by a material such as an elastic body which is hard to propagate sound. Also, in addition to the placement of the absorber 16, the measurement light may be repeatedly deflected along the light path, thereby efficiently preventing it from returning to the measurement sample 9.

Since the measurement light is absorbed by ozone which is generated in oxygen, the optical system 4 or the like are disposed in the housing 2 purged with nitrogen.

Figure 9:
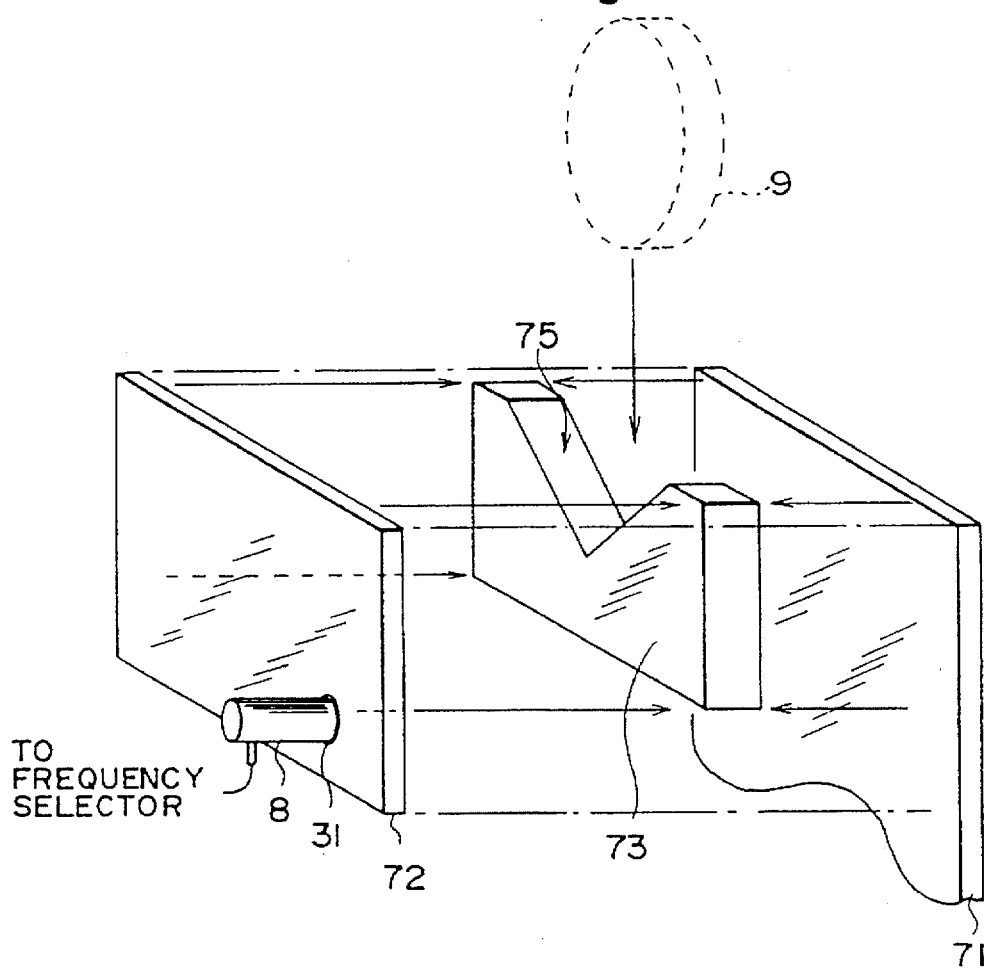
FIG. 9 is a view for explaining a step for assembling a second application of the sample holder shown in FIG. 3.
Figure 10:
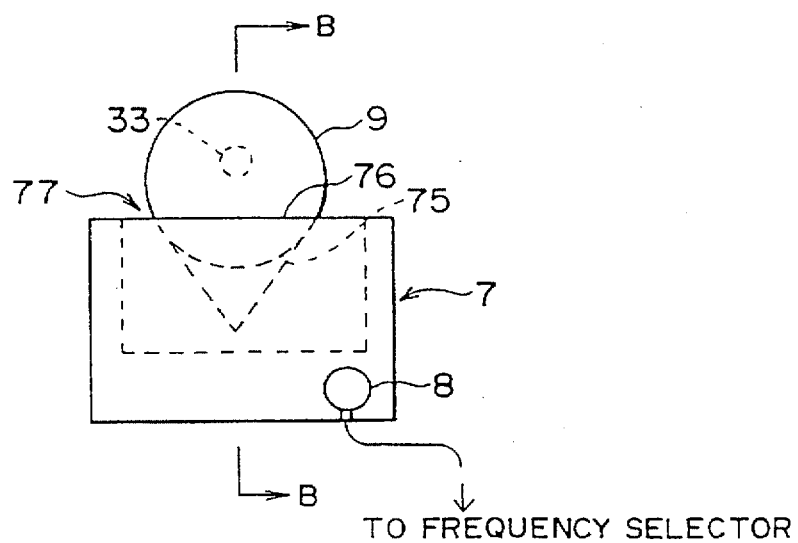
FIG. 10 is a view showing a configuration of the second application of the sample holder shown in FIG. 3 obtained by way of the assembling step of FIG. 9.

The sample holder used is obtained when, as shown in FIGS. 9 and 10, the quartz glass plate 73 having a V-shaped groove is held between the quartz glass plate 71 and the quartz glass plate 72, to which the acoustic sensor 8 is attached by means of the adhesive 31, and then they are bonded and fixed together.

The acoustic signal was detected by the sensor 8 comprising PZT (lead zirconate titanate), which is a piezoelectric material, and a receiver plate made of alumina attached thereto. The sensor 8 (an example of the acoustic sensor) was fixed to the holder body 7 (quartz glass plate 72) by means of the heat-sensitive adhesive 31.

Figure 11:
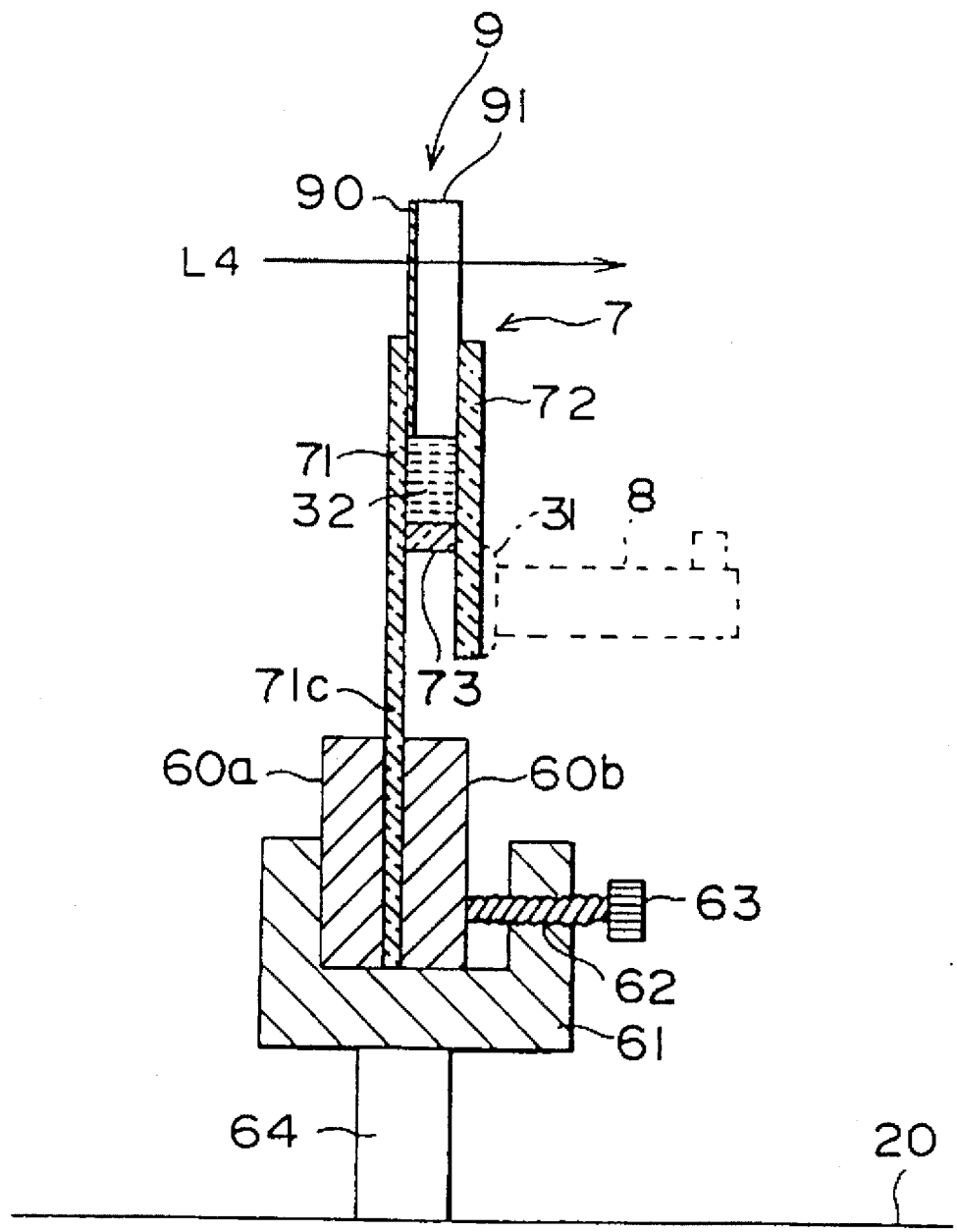
FIG. 11 is a view showing a first supporting mechanism for fixing the sample holder shown in FIG. 10 to a predetermined position within a housing.

As shown in FIG. 11, the part 71c of the holder body 7 is inserted into an optical holder 61 by way of rubber plates 60a and 60b, while being fixed by a pressure screw 63 which engages with a thread groove 62 formed in the optical holder 61. It is fixed by the rubber plates 60a and 60b, which are elastic bodies, in order to acoustically separate the holder body 7 and the optical holder 61 or the like from each other as much as possible (in order to reduce the influence, as noise, upon the acoustic detection). This optical holder 61 is disposed at a bottom surface 20 of the housing 2 by way of a supporting member 64. According to this configuration, the measurement sample 9 is disposed at a predetermined position within the housing 2. Here, FIG. 11 is a view showing the disposition and configuration of the sample holder within the housing 2, including the cross-sectional view of the holder body 7 along line B—B of FIG. 10.

The measurement sample 9 is constituted by the quartz glass substrate 91 (a member capable of transmitting the measurement light therethrough), which has a circular pellet form with a diameter of 30 mm and a thickness of 2 mm, and the thin film 90 formed thereon with a thickness of 1 µm or less, which is an object to be measured. It steadily fits into the V-shaped groove of the sample supporting section 77, whose width (in incident direction L4 of the measurement light) has been set to just 2 mm. Namely, the measurement sample 9 is always set at a predetermined position of the sample supporting section 77.

Into the gap between the depression 75 and the measurement sample 9, Isopar (product name, manufactured by Exxon Chemical International Inc.), which is a non-conductive solvent, is injected, as depicted by 32, by means of the injector 50 till it overflows the opening 76 of the sample supporting section 77. Isopar is used as a solvent for liquid ink or the like. It has a low viscosity such that bubbles are hard to occur therein, while having a low volatility.

The measurement sample 9 thus set at the depression 75 of the sample supporting section 77 was irradiated with light while the zoom lens of the optical system 4 was driven to change the light intensity, and the output (voltage) of the light intensity monitor was measured.

About 15 µsec after the irradiation of the measurement light, the photoacoustic signal is generated upon absorption of the light by the sample 90. Since the signals obtained immediately after the irradiation or those obtained at some time after the acoustic signal has reached the acoustic sensor 8 carry noise signals other than the signals attributable to the optical absorption of the sample 90, about 10 µsec of signals obtained about 15 µsec to about 25 µsec after the irradiation of the measurement light were captured so as to measure the optical absorption.

The signal 15 obtained from the acoustic sensor 8 is appropriately filtered through the frequency selector 14 (having a signal amplifying function), whereby noises are eliminated therefrom. In this experiment, the main frequency of the acoustic signal was about 150 kHz. Accordingly, a wavelength in the vicinity thereof was selected and measured.

By means of the computer 3 (which outputs the control signal 12) controlling the zoom lens within the lens optical system 4, the acoustic signal 16 from the frequency selector 14 and the light intensity signal 13 from the light intensity monitor 11 are measured and recorded per one pulse of irradiation by the light source 1.

Figure 12:
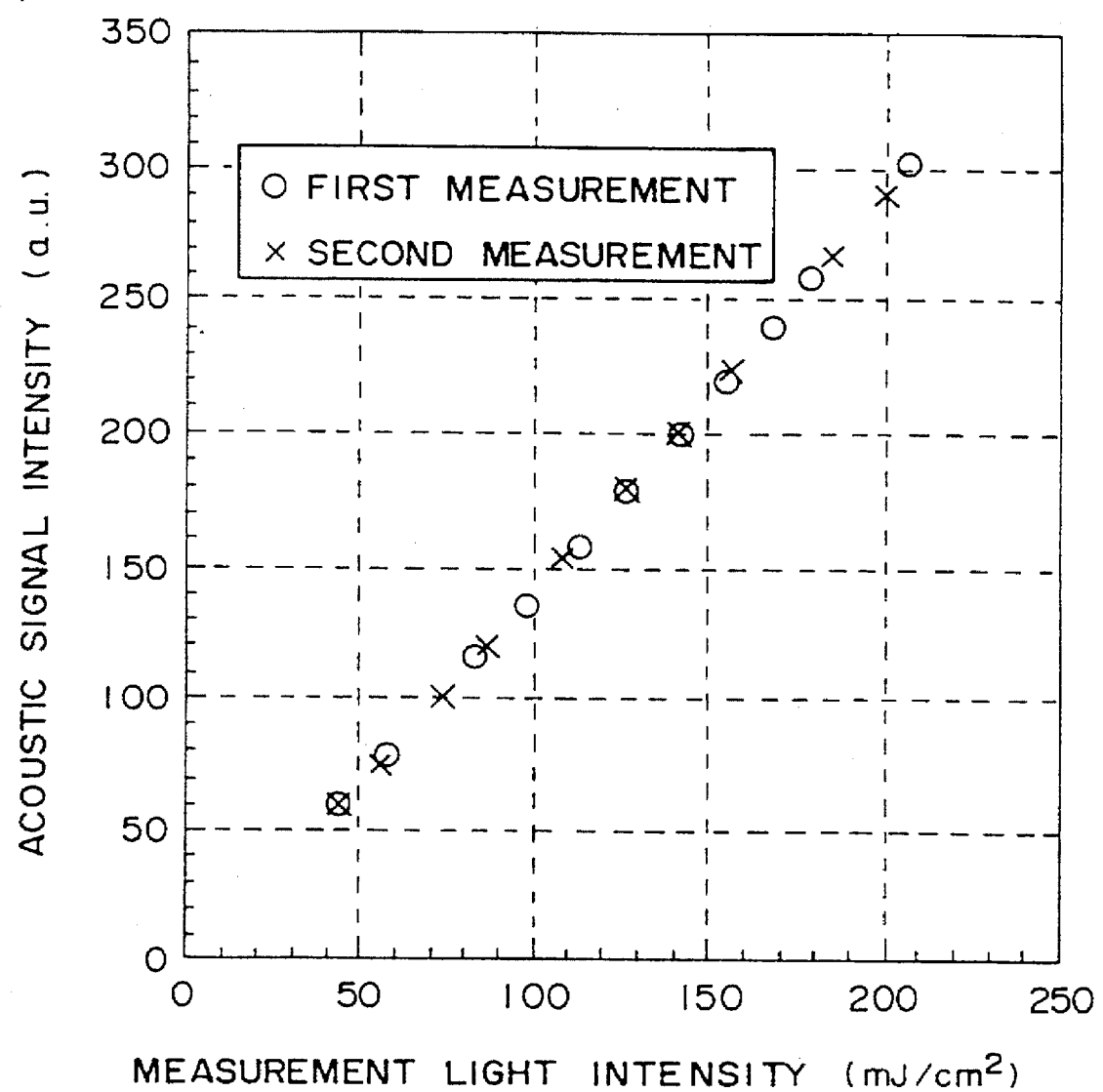
FIG. 12 is a graph showing a result of optical absorption measurement in which the sample holder (FIG. 10) supported within the housing as shown in FIG. 11 is used.

FIG. 12 shows the result of measurement in which the measurement sample 9 comprising a thin film (sample 90), whose absorption at the wavelength of the measurement light was about 5%, formed on a substrate (glass substrate 91) was set in the sample holder (holder body 7) of this embodiment, while the measuring apparatus of FIG. 1 was used.

In FIG. 12, the graph indicating the relationship between the incident light intensity and the acoustic signal intensity is linear, while the gradient of this graph represents an absorption coefficient. When the measurement samples each having the identical sample on the associated glass plate were exchanged, their measured values were on the same line as depicted (the results of the third or later measurement being similar thereto), thereby proving that the optical absorption measurement by means of the sample holder of this embodiment was excellent in reproducibility.

Figure 13:
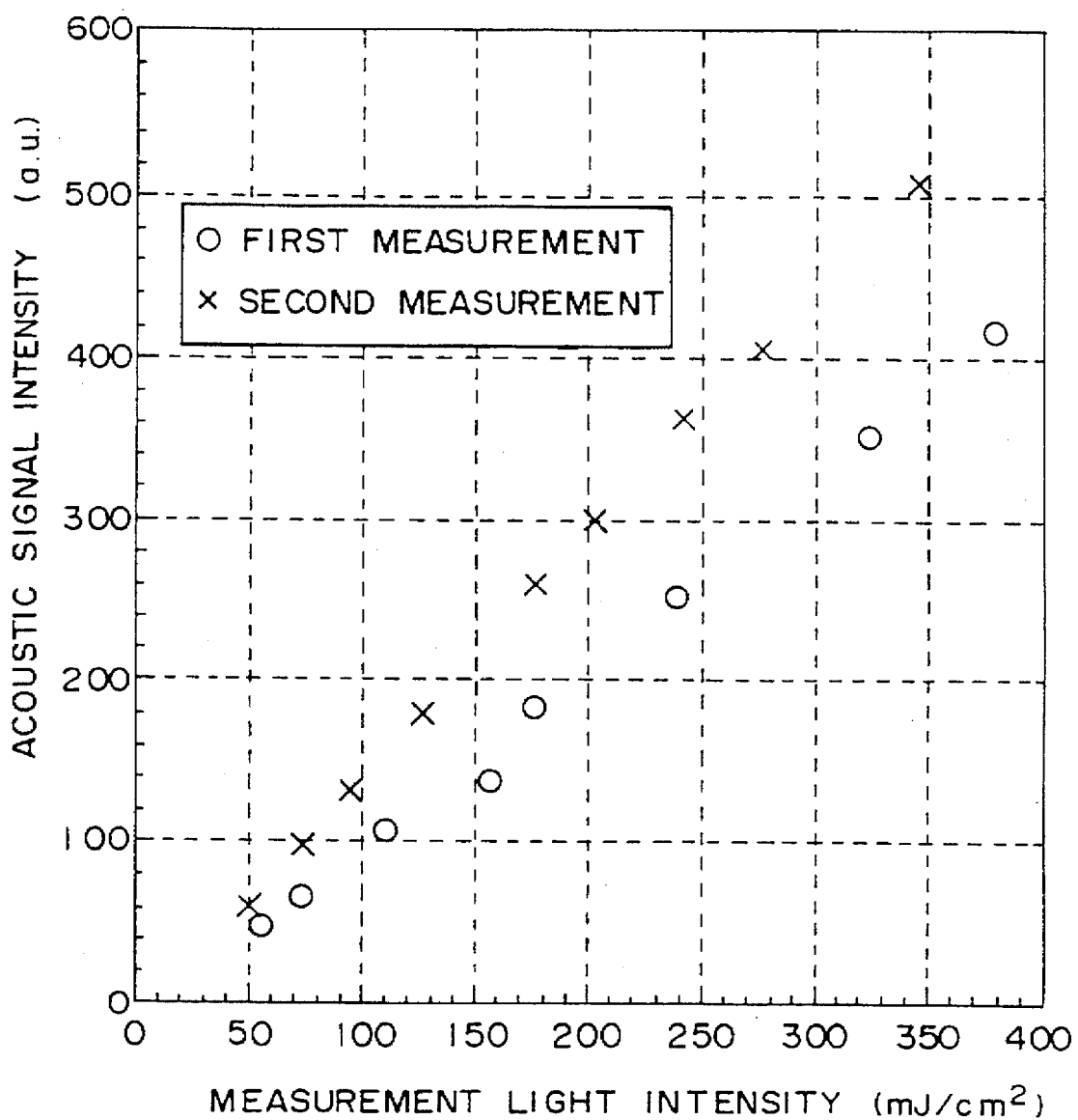
FIG. 13 is a graph showing a result of optical absorption measurement in which grease is used in place of the liquid used in the optical absorption measurement shown in FIG. 12.

FIG. 13 shows the result of experiment in which the measurement sample 9 was set, by way of silicone grease, in the holder body 7 made of aluminum. Also in this experiment, a plurality of optical absorption measuring operations were performed, while the measurement samples having the identical sample 90 were exchanged.

When these results (FIGS. 12 and 13) are compared with each other, it can be seen that the optical absorption measurement using the sample holder of this embodiment is quite excellent in reproducibility.

Also, the measurement sample 9 taken out of the holder body 7 could be cleaned when simply being wiped with a small amount of alcohol or the like. Such a treatment was quite simpler than that needed when grease or the like was used as a matching material. Namely, when grease is attached to the measurement sample 9, a considerable washing process is necessary for removing it.

EXPERIMENT 2

Figure 14:
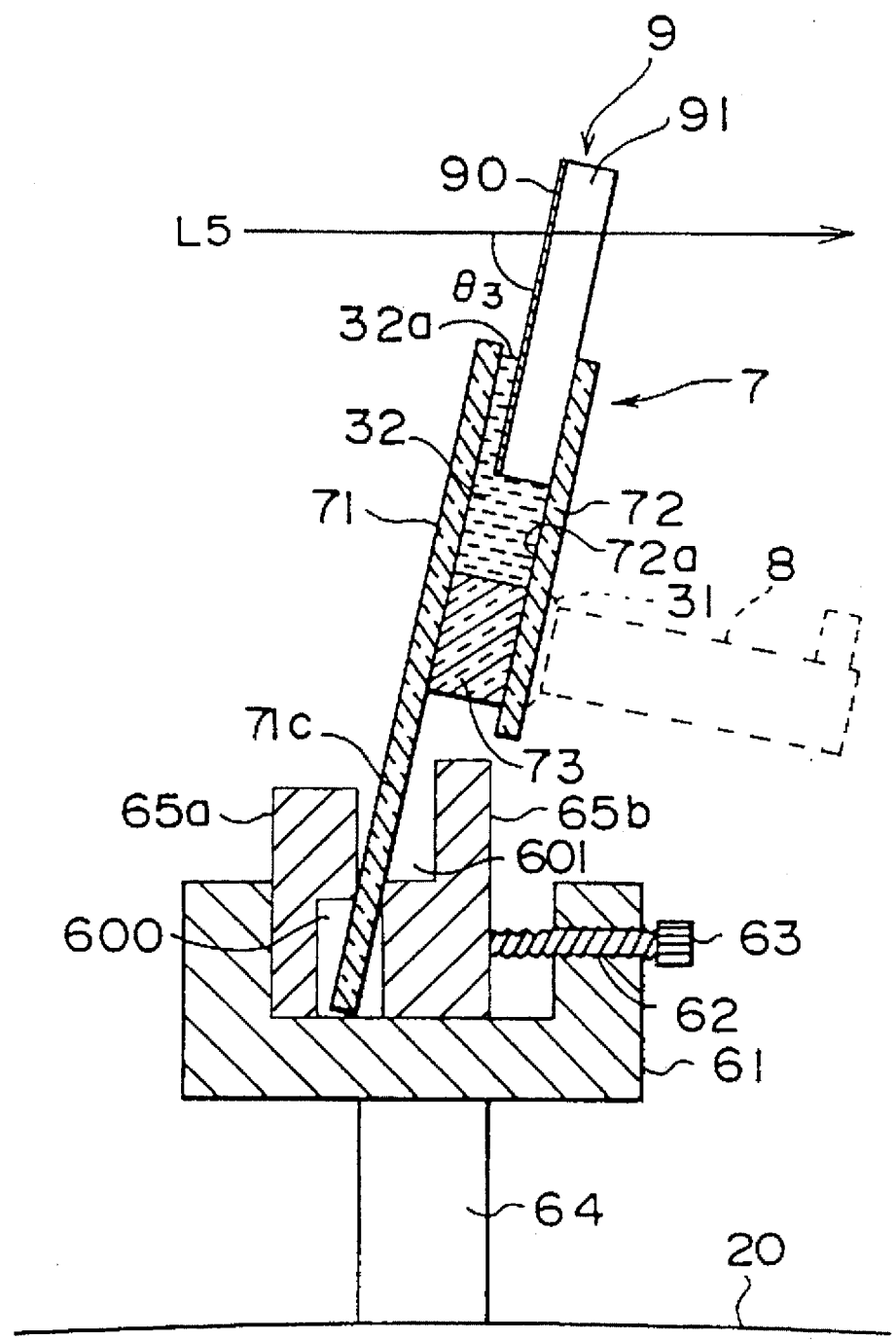
FIG. 14 is a view showing a second supporting mechanism for fixing the sample holder shown in FIG. 10 to a predetermined position within a housing.

FIG. 14 is a view showing a state of disposition of the sample holder in accordance with the present invention, which is different from that of FIG. 11. The depression 75 of the holder supporting section 77 has a width slightly larger than that of the depression 75 shown in FIG. 11, whereas the position of the measurement sample 9 is defined by the surface of the V-shaped groove and the surface 72a. While the holder body 7 was set in the optical holder 61 by way of rubber plates 65a and 65b so as to be inclined by a predetermined angle $\theta_3$ with respect to incident direction L5 of the measurement light, measurement was performed similarly.

In this case, the measurement sample 9 is easily set so as to come in contact with the back surface of the depression 75. After the measurement sample 9 is set, Isopar is injected by the injector 50 till it overflows (see FIG. 5).

Figure 15:
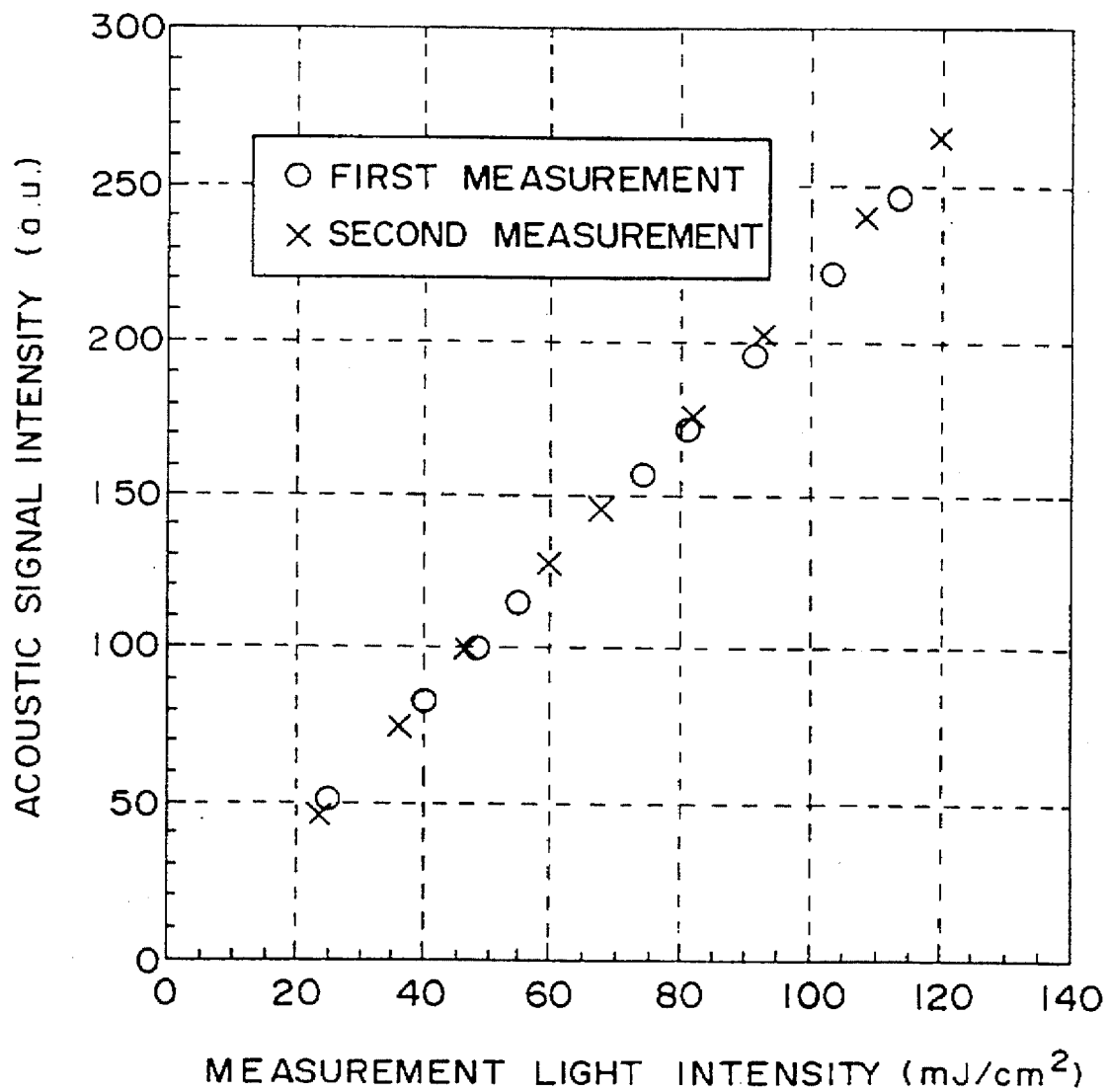
FIG. 15 is a graph showing a result of optical absorption measurement in which the sample holder (FIG. 10) supported within the housing as shown in FIG. 14 is used.

FIG. 15 shows the result of measurement. In terms of reproducibility in signals when the measurement sample 9 was exchanged for another one, favorable results similar to those of the above-mentioned Experiment 1 were obtained.

In the foregoing experiments, a measurement system irradiating a pulse laser with a single wavelength is shown as an example thereof. However, for example, a measurement system intermittently irradiating a continuously oscillating laser may be applied to the measuring apparatus in accordance with the present invention.

As explained in the foregoing, the sample holder for the optical absorption measuring apparatus of the present invention can constantly hold the acoustic contact condition of the solid sample 91 and the acoustic sensor 8 with respect to each other in a simple manner, thereby improving the reliability and efficiency in the optical absorption measurement.

Figure 16:
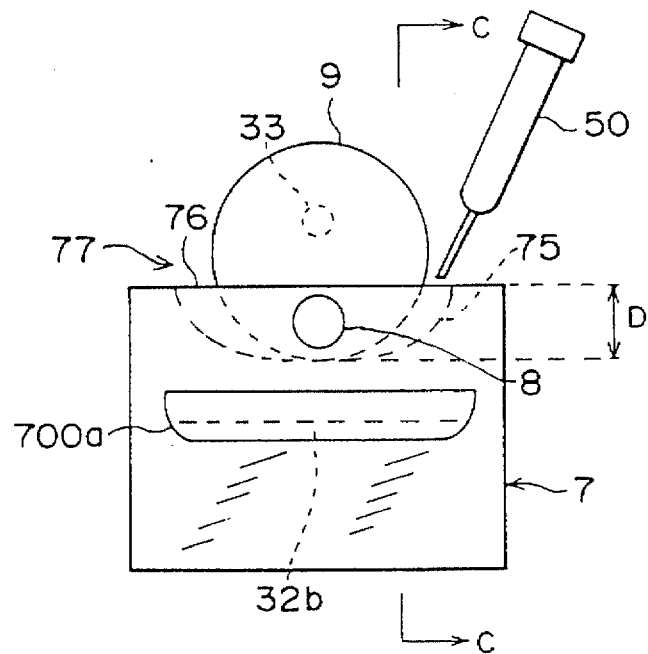
FIG. 16 is a view showing a configuration of a second embodiment of the sample holder in accordance with the present invention.
Figure 17:
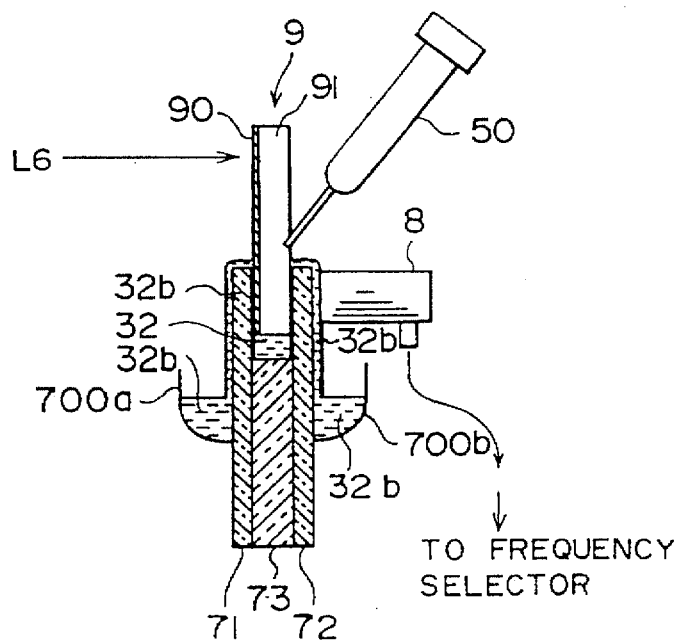
FIG. 17 is a view showing a cross-sectional configuration of the second embodiment of the sample holder along line C—C in FIG. 16.

In the following, a second embodiment of the sample holder in accordance with the present invention will be explained. As shown in FIGS. 16 and 17, the basic configuration of the second embodiment is the same as that of the first embodiment shown in FIGS. 3 and 4.

The measurement sample 9 held in the sample holder (holder body 7) of FIGS. 16 and 17 includes the glass substrate 91 and the thin-film sample 90 formed on the glass substrate 91. The substrate 91 is made of a predetermined material with a predetermined size, while having a sufficiently smooth substrate surface. Preferably, the amount of measurement light absorbed by the substrate 91 is sufficiently smaller than the amount of measurement light absorbed by the thin-film sample 90 to be measured. In this embodiment, the glass substrate is formed like a circular pellet.

The sample holder of the second embodiment comprises, for example as shown in FIGS. 16 and 17, the liquid supplying mechanism 50 and liquid containers 700a and 700b (liquid recovering mechanism) as a liquid amount adjusting system.

As in the case of the sample holder shown in FIG. 3, the sample holder of FIG. 16 comprises the depression 75 (an example of the sample supporting section 77) having an arc-like bottom surface, while the depression 75 has such a maximum depth D that the upper portion (portion 33 to be irradiated with light) of the measurement sample 9 is placed above the opening 76 of the sample supporting section 77 when the measurement sample 9 is set in the depression 75.

Also, into the depression 75, the liquid 32 (matching material) is injected by the liquid supplying mechanism 50 such that the gap between the measurement sample 9 and the surface defining the depression 75 is filled therewith. As the liquid 32, a liquid having such a specific gravity that the measurement sample 9 does not rise to the surface thereof is used. Also, of the measurement sample 9, the portion 33 which is not immersed in the liquid 32 is irradiated with the measurement light. Here, arrow L6 indicates the incident direction of the measurement light. Also, FIG. 17 is a cross-sectional view of the holder body 7 along line C—C of FIG. 16.

As the liquid supplying mechanism included in the liquid amount adjusting system of the second embodiment, the injector 50 shown in FIGS. 5 and 16 may be used, for example, though it should not be restricted thereto (and other examples will be explained later). Here, the injector 50 can minutely control the amount of the liquid to be supplied, while having a function to eliminate the excess liquid when the amount of supply is too much (liquid recovering mechanism).

In any case, when a marking for monitoring the liquid amount is effected within the depression 75, the optical absorption can be measured with a predetermined liquid amount.

However, in this method, each time the measurement sample 9 is exchanged for another one, it is necessary to completely evacuate the liquid from the depression 75 and then fill the depression 75 with a predetermined amount of the liquid, thereby complicating the manipulation thereof. Also, even when the supplying amount or removing amount of the liquid can be minutely controlled by the injector 50, the manipulation becomes difficult due to the influence of the dripping or capillary phenomenon when the liquid 32 has a low viscosity.

Accordingly, in order to easily attain a constant amount of the liquid 32 with which the depression 75 is filled, the second embodiment realizes a configuration such that the liquid 32 is supplied from the liquid supplying mechanism with an amount greater than the liquid amount by which the depression 75 becomes full, while the unnecessary (excess) liquid 32b of the supplied liquid 32 is naturally accommodated in the liquid containers 700a and 700b.

In order to naturally accommodate the unnecessary (excess) liquid 32b into the liquid containers 700a and 700b, as shown in FIG. 17, for example, the unnecessary (excess) liquid 32b is made to naturally overflow the opening 76 of the sample supporting section 77, such that thus overflowed liquid 32b is accommodated in the liquid containers 700a and 700b disposed at the wall surface of the holder body 7. Here, in this configuration, the opening 76 functions to define the liquid level 32a of the liquid 32 (as a liquid level adjusting mechanism).

Preferably, the unnecessary (excess) liquid 32b accommodated in the liquid containers 700a and 700b is collected in another vessel when appropriate or continuously, since the liquid containers 700a and 700b can be prevented from becoming full of the liquid 32b thereby. For example, the liquid recovering mechanism shown in FIG. 19 collects the liquid 32b retained in the liquid container 700a, in the direction of R2, through a pipe 510 connected to the liquid container 700a.

When the unnecessary (excess) liquid 32b is simply made to overflow the depression 75 of the sample supporting section 77, the overflowed liquid 32b remains adhering to various places. This state may cause, due to the uncleanness of the measuring apparatus, deterioration in performance, unfavorable influence upon environment, waste of liquid, or the like. In the sample holder in accordance with the present invention, by contrast, the above-mentioned state does not occur since the overflowed liquid 32b is accommodated in the liquid containers 700a and 700b.

Here, the inventors have confirmed that, though the liquid 32b may adhere to a part of the wall surface of the holder body 7 even when the overflowed liquid is accommodated in the liquid containers 700a and 700b, the acoustic signal is not influenced thereby.

The liquid 32b adhering to a part of the wall surface of the holder body 7 may be wiped out when necessary. In the case where the liquid 32 is easy to evaporate, it is unnecessary to wipe it out since it naturally evaporates after adhesion.

Even in the case where the depression 75 is initially filled with a predetermined amount of the liquid 32, the latter slightly decreases when the measurement sample 9 is exchanged for another one or during the measurement using a liquid with a high volatility. Accordingly, the measuring apparatus in accordance with the present invention comprises a liquid amount adjusting system for adjusting the liquid 32 filled in the depression 75 to a constant or substantially constant value always during the measurement.

In particular, the liquid supplying mechanism in this liquid amount adjusting system preferably has a function to supply the liquid such that the liquid 32 filled in the depression 75 always becomes constant or substantially constant during the measurement.

Figure 18:
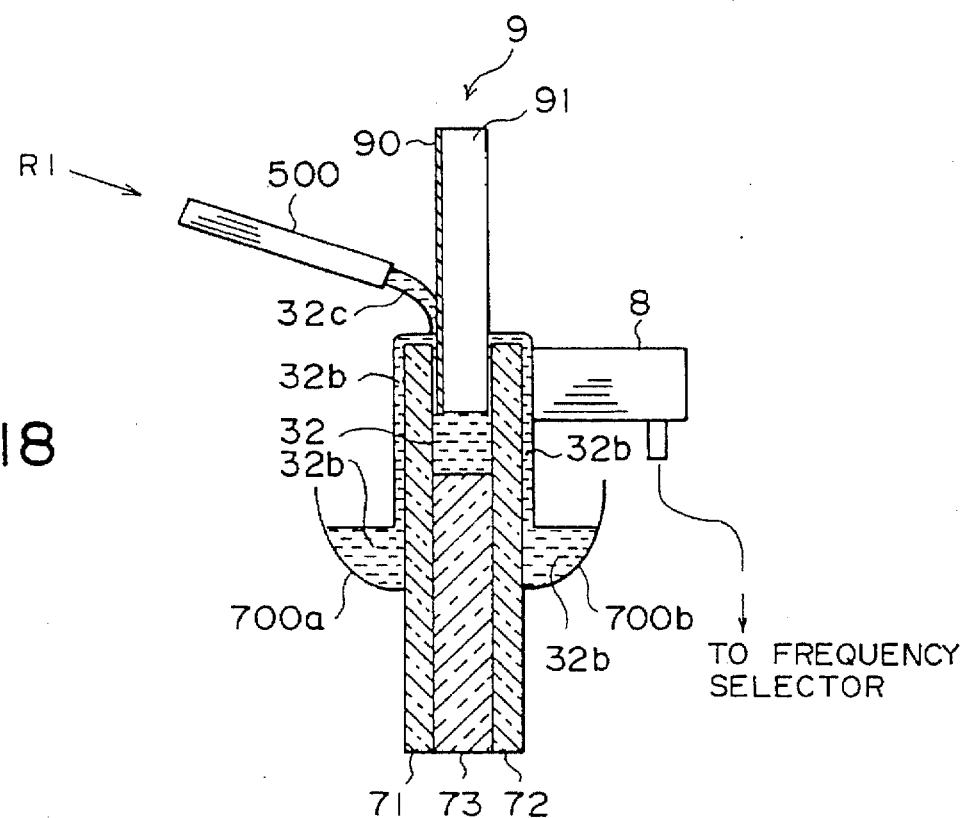
FIG. 18 is a view showing a liquid supplying mechanism of a liquid amount adjusting system.
Figure 19:
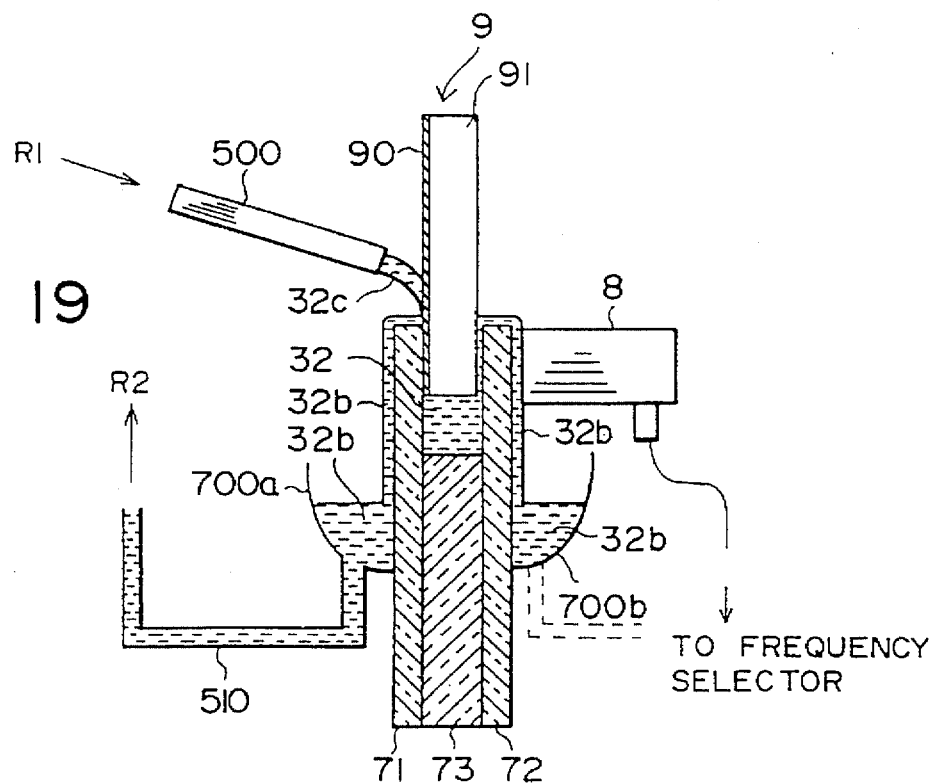
FIG. 19 is a view showing a liquid supplying mechanism and a liquid recovering mechanism of a liquid amount adjusting system.

As shown in FIGS. 18 and 19, applications of such a mechanism include an influx mechanism utilizing gravity, a siphon mechanism, and an influx mechanism based on application of pressure.

The liquid supplying mechanism shown in FIGS. 18 and 19 constantly maintains the amount of the liquid 32 within the depression 75 by making a supplementary liquid 32c flow in the direction of R1 by way of a pipe 500.

When the liquid 32 is supplied (filled or supplemented) into the depression 75, it is preferably supplied with a flow rate or by way of a flow path such that bubbles due to the liquid flow or a large swell on the liquid level, which may inhibit the acoustic propagation, do not occur.

In particular, in order to efficiently utilize the liquid used or further prevents the environment and the performance of the apparatus from deteriorating, in addition to the above-mentioned liquid supplying mechanism, a liquid recovering mechanism for collecting the liquid 32b accommodated in the liquid containers 700a and 700b is disposed such that the collected liquid can be supplied to the depression 75.

Since the acoustic propagation characteristic changes due to the temperature of a material, the temperature of the measurement system is preferably held as constantly as possible in order to perform accurate measurement. Accordingly, the measuring apparatus in accordance with the present invention is preferably provided with a liquid temperature control system which controls the temperature of the liquid used (see FIGS. 21 and 22).

In the second embodiment, the acoustic signal is detected, for example, by the piezoelectric element 8 (an example of the acoustic sensor) such as that shown in FIG. 16 attached to the holder body 7.

The piezoelectric element 8 of this embodiment is firmly fixed to the holder body 7 by means of the adhesive 31 or the like. Accordingly, the acoustic matching is stably attained between the piezoelectric element 8 and the holder body 7, thereby improving the reliability in measurement.

Also in the second embodiment, in order to attain a better reproducibility in the optical absorption measurement, a structure for holding the measurement sample 9 at a predetermined position of the sample supporting section 77, i.e., a positioning mechanism, is provided (see FIGS. 6 to 8).

EXPERIMENT 3

In the following, the result of the photoacoustic measurement performed with the optical absorption measuring apparatus (FIG. 1) to which the sample holder shown in FIGS. 16 and 17 was applied will be explained. The conditions for the experiment explained in the following are similar to those of the above-mentioned first embodiment.

The light source 1 is an ArF excimer laser (with a wavelength of 193 nm) whose pulse width is about 20 nsec. The pulse measurement light is transmitted through the lens optical system 4 and then converged by the objective lens 6 so as to be guided to the measurement sample 9 held by the sample holder fixed to the optical holder 61 (see FIG. 20). The diameter of the measurement light on the sample surface is about 3 mm.

The intensity of the measurement light is adjusted by a zoom lens inserted into the optical system 4. Also, the intensity of the measurement light is monitored by the light intensity monitor 11 (bi-planar type photomultiplier) which is disposed at a branch light path formed due to the reflection effected by the quartz glass plate 5.

The light transmitted through the measurement sample 9 is blocked by the absorber 16 such that it is prevented from returning to the measurement sample 9. Here, the absorber is preferably constituted by a material such as an elastic body which is hard to propagate sound. Also, in addition to the placement of the absorber 16, the measurement light may be repeatedly deflected along the light path, thereby efficiently preventing it from returning to the measurement sample 9.

Since the measurement light is absorbed by ozone which is generated in oxygen, the optical system 4 or the like are disposed in the housing 2 purged with nitrogen.

Figure 20:
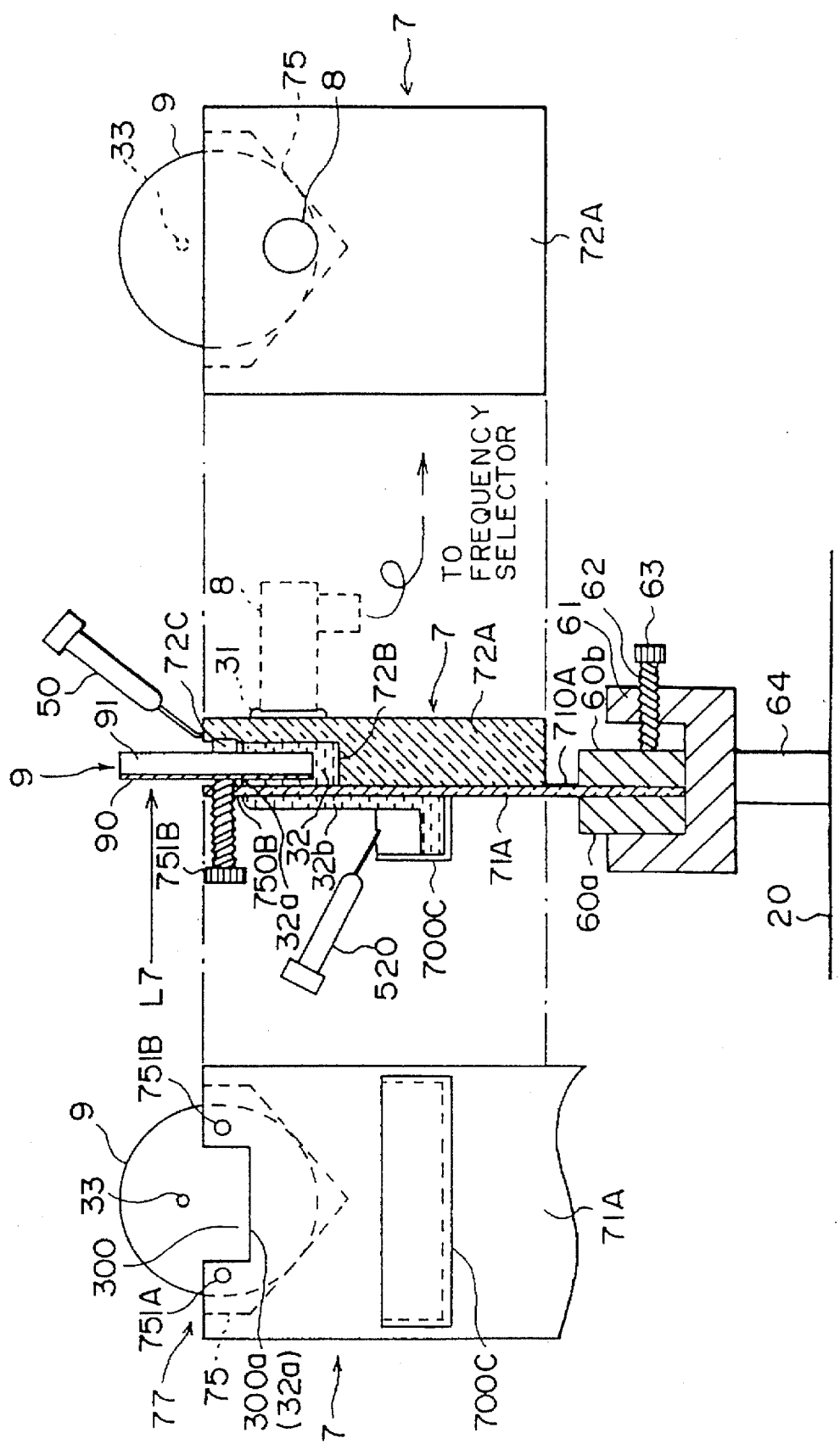
FIG. 20 is a view showing an application of the sample holder shown in FIG. 16.

As shown in FIG. 20, the sample holder is a holder made of aluminum provided with the depression 75 having a V-shaped bottom surface. Here, differently from the first embodiment, the holder body 7 of the second embodiment is constituted by two aluminum members 71A and 72A.

The acoustic signal was detected by the sensor 8 comprising PZT (lead zirconate titanate), which is a piezoelectric material, and a receiver plate made of alumina attached thereto. The sensor 8 (an example of the acoustic sensor) was fixed to the holder body 7 by means of the heat-sensitive adhesive 31.

As shown in FIG. 20, a supporting portion 710A of the holder body 7 is inserted into the optical holder 61 by way of the rubber plates 60a and 60b, while being fixed by the pressure screw 63 which engages with the thread groove 62 formed in the optical holder 61. It is fixed by the rubber plates 60a and 60b, which are elastic bodies, in order to acoustically separate the holder body 7 and the optical holder 61 or the like from each other as much as possible (in order to reduce the influence, as noise, upon the acoustic detection).

The measurement sample 9 is constituted by the quartz glass substrate 91 (material capable of transmitting the measurement light therethrough), which has a circular pellet form with a diameter of 30 mm and a thickness of 2 mm, and the thin film sample 90 formed thereon with a thickness of 1 μm or less. This measurement sample 9 is set into the depression 75 having a V-shaped bottom surface in the sample supporting section 77 and fixed to a predetermined position as being held between screws 751A and 751B and a spacer 72C disposed at one wall.

Into the gap between the surface of the depression 75 and the measurement sample 9, Isopar (product name, a matching material manufactured by Exxon Chemical International Inc.), which is a non-conductive solvent, is injected, as depicted by 32, by means of the injector 50 (an example of the liquid supplying mechanism) till it overflows the guiding section 300 provided with the member 71A. Isopar is used as a solvent for liquid ink or the like. It has a low viscosity such that bubbles are hard to occur therein, while having a low volatility. Also, this guiding section 300 functions as a liquid level adjusting mechanism, whereas the edge 300a of the guiding section 300 coincides with the liquid level 32a of the liquid 32 within the depression 75.

The liquid 32b overflowed the depression 75 by way of the guiding section 300 descends along the wall of the holder body 7 so as to be accommodated in the liquid reservoir 700c (an example of the liquid container). Here, since the front wall (member 71A) of the holder body 7 has a height smaller than that of the rear wall (member 72A), the liquid 32 overflows only from the front wall side (guiding section 300a).

The measurement sample 9 thus set within the depression 75 of the sample supporting section 77 is irradiated with light while the zoom lens of the optical system 4 is driven to change the light intensity, and the output (voltage) of the light intensity monitor 11 is measured. Here, in this experiment, the injector 50 is used as a liquid supplying mechanism, while an injector 520 is used as a liquid recovering mechanism.

About 15 μsec after the irradiation of the measurement light, the photoacoustic signal is generated upon absorption of the light by the sample 90. Since the signals obtained immediately after the irradiation or those obtained at some time after the acoustic signal has reached the acoustic sensor 8 carry noise signals other than the signals attributable to the optical absorption of the sample 90, about 10 μsec of signals obtained about 15 μsec to about 25 μsec after the irradiation of the measurement light were collected so as to measure the optical absorption.

The signal 15 obtained from the acoustic sensor 8 is appropriately filtered through the frequency selector 14 having a signal amplifying function, whereby noises are eliminated therefrom. In this experiment, the main frequency of the acoustic signal was about 150 kHz. Accordingly, a wavelength in the vicinity thereof was selected and measured.

By means of the computer 3 (which outputs the control signal 12) controlling the zoom lens within the lens optical system 4, the acoustic signal 16 from the frequency selector 14 and the light intensity signal 13 from the light intensity sensor 11 are measured and recorded per one pulse of irradiation by the light source 1.

As a result of the measurement, even when the liquid 32 descended along the front wall of the holder body 7 and further when the thus descended unnecessary liquid 32b was accommodated in the liquid container 700c, since the liquid amount within the depression 75 in the sample supporting section 77 did not change, no change was observed in the photoacoustic signal. Also, a favorable reproducibility in measurement was observed even when the measurement sample 9 was exchanged for another one.

Here, the liquid was supplemented by means of the injector 50 (included in liquid supplying mechanism) when appropriate such that the liquid amount within the depression 75 did not decrease. Also, the liquid 32b accommodated in the liquid container 700c was collected by means of the injector 520 (included in liquid recovering mechanism) when appropriate. Accordingly, most of the overflowed liquid 32b was collected, whereby hands and the measuring apparatus were prevented from becoming dirty.

Therefore, the second embodiment yielded greatly advantageous effects in terms of efficiently utilizing the liquid and preventing the environment and the performance of the apparatus from deteriorating.

EXPERIMENT 4

Figure 21:
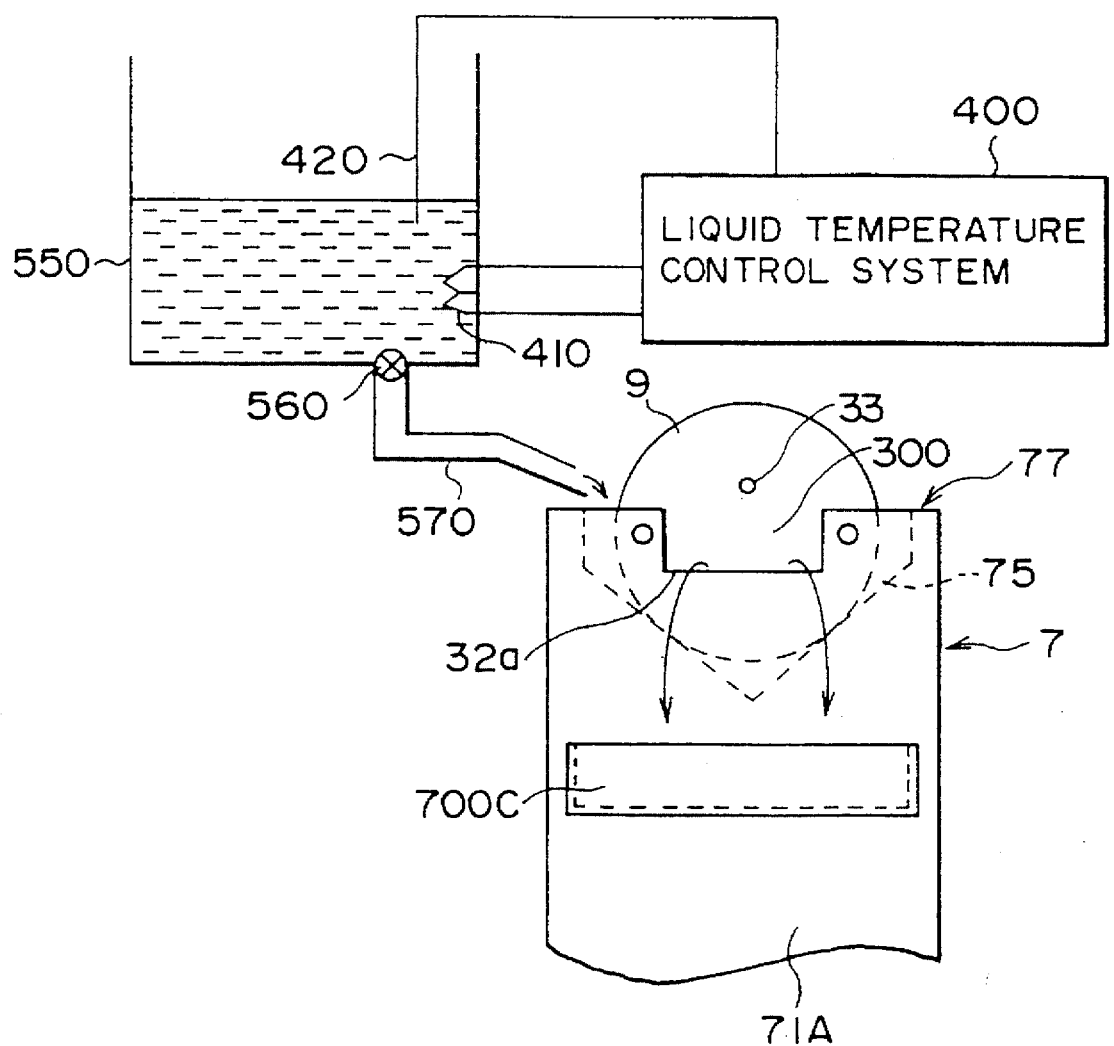
FIG. 21 is a view showing configurations of a liquid amount adjusting system (including a liquid supplying mechanism and a liquid level adjusting mechanism) and a liquid temperature control system.

In this experiment, as shown in FIG. 21, measurement similar to that of Experiment 3 was performed in a configuration in which the depression 75 of the sample supporting section 77 was filled with a liquid matching material (methyl alcohol) from a liquid supplying vessel 550 (an example of a liquid supplying mechanism and a liquid supplementing mechanism) equipped with a liquid supplying tubing 570 and a valve 560, while the depression 75 was continuously supplemented with the liquid 32 during the measurement. The other features in the configuration were the same as those of Experiment 3.

When the depression 75 was being filled and supplemented with the liquid 32, the flow rate was controlled by conductance control in the liquid supplying tubing 570 by means of the valve 560 such that the liquid flow generated no bubbles.

In this experiment, the depression 75 could be continuously supplemented with the liquid 32 during measurement. Accordingly, even when methyl alcohol, whose liquid amount was likely to decrease due to its high volatility, was used, the photoacoustic signal exhibited no change since the liquid amount in the depression 75 of the sample supporting section 77 did not change. Also, a favorable reproducibility in measurement was observed when the measurement sample 9 was exchanged for another one.

Here, in the configuration of FIG. 21, when the measurement sample 9 is to be exchanged for another one, the valve 560 can be closed so as to stop supplying the liquid 32.

Also, since methyl alcohol attached to the measurement sample 9 and the holder body 7 immediately evaporated, it was unnecessary to wipe it out.

Preferably, in the configuration of FIG. 21, in order to constantly maintain the temperature of the liquid stored in the tank 550, a liquid temperature control system 400 is provided. This liquid temperature control system 400 includes at least a temperature sensor 420 and a heater 410.

EXPERIMENT 5

Figure 22:
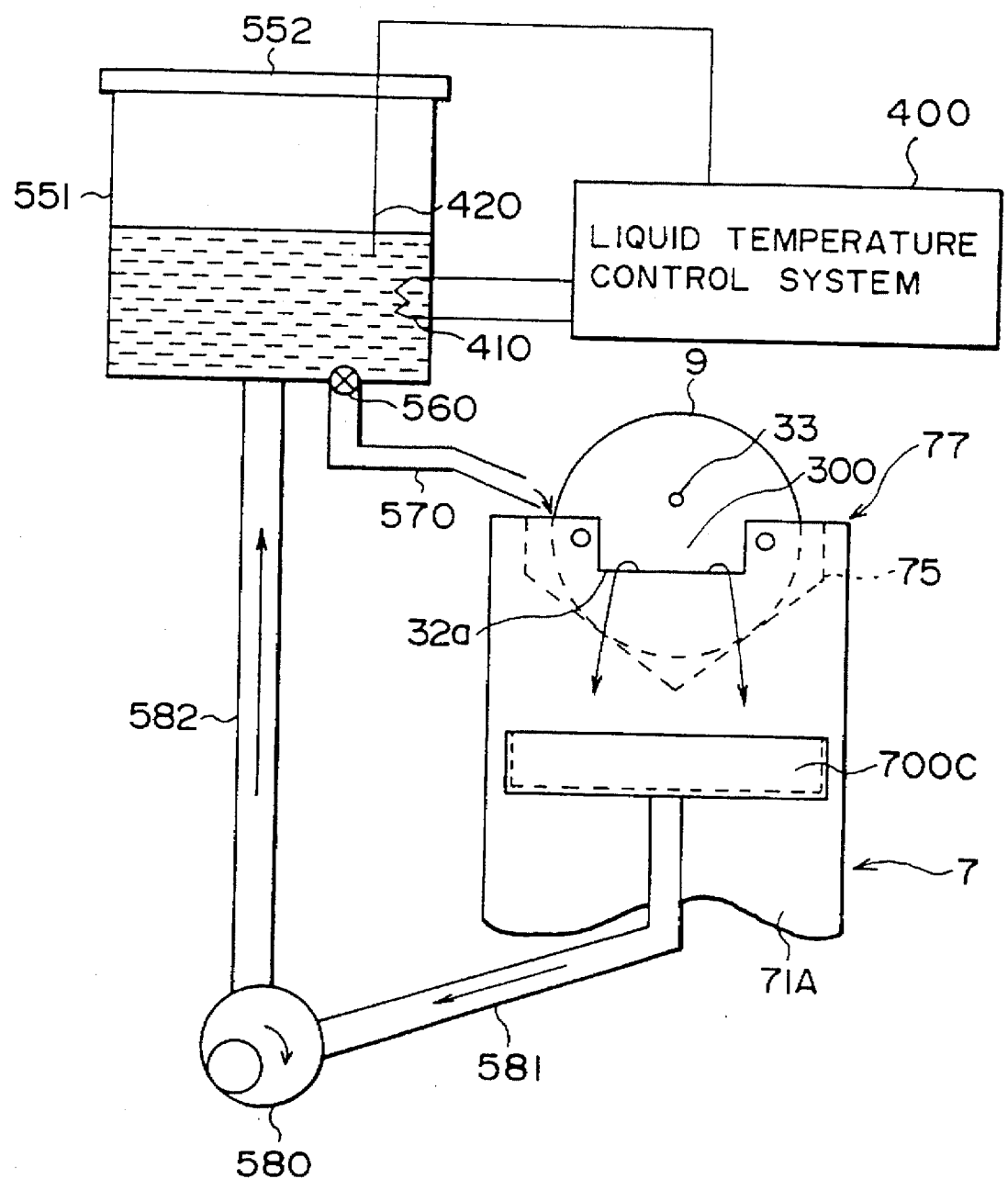
FIG. 22 is a view showing configurations of a liquid amount adjusting system (including a liquid supplying mechanism, a liquid level adjusting mechanism, and a liquid recovering mechanism) and a liquid temperature control system.

In this experiment, as shown in FIG. 22, measurement was performed in a manner similar to that of Experiment 4 except that a liquid supplying vessel 551 (an example of a liquid supplying mechanism and a liquid supplementing mechanism) equipped with the liquid supplying tubing 570 and the valve 560 further included a liquid recovering mechanism for collecting the liquid accommodated in the liquid container 700c so that thus collected liquid could be supplied to the depression 75 of the sample supporting section 77 and that a lid 552 was attached to the liquid supplying vessel 551 so as to reduce the exposure of the liquid within the container 551 to the atmosphere, thereby approximating a sealed state.

The liquid recovering mechanism is constituted by a pump 580 and pipes 581 and 582 respectively connecting the pump 580 to the liquid container 700c and the liquid supplying vessel 551.

In this experiment, the supply (filling and supplement) and circulation of the liquid could be effected in a full-automatic manner, whereby further advantageous effects were obtained in efficiently utilizing the liquid and preventing the environment and the performance of the apparatus from deteriorating.

Preferably, also in the apparatus shown in FIG. 22, the liquid temperature control system 400 including the temperature sensor 420 and the heater 410 is provided.

As explained in the foregoing, in accordance with the optical absorption measuring apparatus of the present invention, the acoustic contact condition of the measurement sample 9 and the holder body 7 or the like with respect to each other can be constantly held in a simple manner, whereby reliability and efficiency in the optical absorption measurement can be improved.

Also, the optical absorption measuring apparatus of the present invention can yield greatly advantageous effects in efficiently utilizing the liquid matching material used for measurement and in preventing the environment and the performance of the apparatus from deteriorating.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

The basic Japanese Applications No. 160312/1995 filed on Jun. 27, 1995 and No. 288304/1995 filed on Nov. 7, 1995 are hereby incorporated by reference.

What is claimed is:

1. A sample holder applicable to an apparatus which measures an optical absorption of a sample with respect to measurement light having a predetermined wavelength by photoacoustic measurement, said sample holder comprising:

a holder body having a sample supporting section which saves a predetermined amount of a liquid and supports the sample while a part of the sample is immersed in the liquid, said sample supporting section having an opening through which a part of the sample to be irradiated with the measurement light is placed above a liquid level of the liquid;

an acoustic sensor for detecting an acoustic signal generated upon a change in volume of the sample occurring due to the optical absorption of the sample irradiated with the measurement light; and a holding mechanism for directly attaching said acoustic sensor to a predetermined position of said holder body.

2. A sample holder according to claim 1, wherein said holding mechanism holds said acousticسسs sensor at a position where said holder body prevents said acoustic sensor from being irradiated with the measurement light.

3. A sample holder according to claim 1, wherein said holding mechanism fixes said acoustic sensor to said predetermined position of said holder body while said holder body and said acoustic sensor are acoustically matched with each other.

4. A sample holder according to claim 1, wherein said holding mechanism fixes said acoustic sensor to said predetermined position of said holder body while the liquid and the acoustic sensor are acoustically matched with each other.

5. A sample holder according to claim 1, wherein said holder body is made of a material whose loss corresponding to absorption and scattering thereof with respect to the measurement light having the predetermined wavelength is 0.1% or less.

6. A sample holder according to claim 1, further comprising an anti-reflection coating provided on a surface of said holder body.

7. A sample holder according to claim 1, further comprising a positioning mechanism for defining a position of the sample.

8. A sample holder according to claim 1, wherein said sample supporting section of said holder body has a surface for defining a position to which the sample is fixed.

9. A sample holder according to claim 1, wherein said sample supporting section of said holder body has a maximum depth by which the portion of the sample to be irradiated with the measurement light is sufficiently placed above the liquid level of the liquid by way of the opening of said sample supporting section.

10. An apparatus which measures an optical absorption of a sample by measuring an acoustic signal generated upon a change in volume of a sample irradiated with measurement light having a predetermined wavelength, said apparatus comprising:

a housing for defining a dark room; and a sample holder according to claim 1 disposed within said housing, said sample holder being located at a position where said sample holder is prevented from being irradiated with the measurement light.

11. An apparatus according to claim 10, further comprising an optical system disposed within said housing and placed in a light path through which the measurement light travels.

12. An apparatus according to claim 10, further comprising an optical monitor for monitoring a light intensity of the measurement light, said optical monitor being disposed within said housing and receiving a part of the measurement light.

13. An apparatus according to claim 10, further comprising a liquid amount adjusting system for constantly holding the liquid level of the liquid to be retained in said sample supporting section of said holder body.

14. An apparatus according to claim 13, wherein said liquid amount adjusting system includes a liquid supplying mechanism for supplying the liquid into said sample supporting section of said holder body.

15. An apparatus according to claim 13, wherein said liquid amount adjusting system includes a liquid recovering mechanism for removing a part of the liquid saved in said sample supporting section of said holder body.

16. An apparatus according to claim 15, wherein said liquid recovering mechanism comprises:
   a liquid level adjusting mechanism for maintaining the liquid level of the liquid while a part of the sample is immersed in the liquid, said liquid level adjusting mechanism being provided at said holder body; and
   a liquid container which is disposed at a predetermined position within said holder body and accommodates, of the liquid saved in said sample supporting section, an unnecessary part of the liquid guided by said liquid level adjusting mechanism.

17. An apparatus according to claim 10, further comprising a liquid temperature control system for controlling the temperature of the liquid to be saved into said sample supporting section of said holder body.

18. A sample holder applicable to an apparatus which measures an optical absorption of a sample with respect to measurement light having a predetermined wavelength by photoacoustic measurement, said sample holder comprising:
   a holder body having a sample supporting section which saves a predetermined amount of a liquid and supports the sample while a part of the sample is immersed in the liquid, said sample supporting section having an opening through which a part of the sample to be irradiated with the measurement light is placed above a liquid level of the liquid;
   a liquid level adjusting mechanism for constantly maintaining the liquid level of the liquid while a part of the sample is immersed in the liquid, said liquid level adjusting mechanism being provided at said holder body; and
   a liquid container which is disposed at a predetermined position of said holder body and accommodates, of the liquid saved in said sample supporting section, an unnecessary part of the liquid guided by said liquid level adjusting mechanism.

19. A sample holder according to claim 18, further comprising:
   an acoustic sensor for detecting an acoustic signal generated upon a change in volume of the sample occurring due to the optical absorption of the sample irradiated with said measurement light; and
   a holding mechanism for directly attaching said acoustic sensor to a predetermined position of said holder body.

20. A sample holder according to claim 19, wherein said holding mechanism holds said acoustic sensor at a position where said holder body prevents said acoustic sensor from being irradiated with the measurement light.

21. A sample holder according to claim 19, wherein said holding mechanism fixes said acoustic sensor to said predetermined position of said holder body while said holder body and said acoustic sensor are acoustically matched with each other.

22. A sample holder according to claim 19, wherein said holding mechanism fixes said acoustic sensor to said predetermined position of said holder body while the liquid and said acoustic sensor are acoustically matched with each other.

23. A sample holder according to claim 18, wherein said holder body is made of a material whose loss corresponding to absorption and scattering thereof with respect to the measurement light having the predetermined wavelength is 0.1% or less.

24. A sample holder according to claim 18, further comprising an anti-reflection coating provided on a surface of said holder body.

25. A sample holder according to claim 18, further comprising a positioning mechanism for defining a position of the sample.

26. A sample holder according to claim 18, wherein said sample supporting section of said holder body has a surface for defining a position to which the sample is fixed.

27. A sample holder according to claim 18, wherein said sample supporting section of said holder body has a maximum depth by which the portion of the sample to be irradiated with the measurement light is sufficiently placed above the liquid level of the liquid by way of the opening of said sample supporting section.

28. An apparatus which measures an optical absorption of a sample by measuring an acoustic signal generated upon a change in volume of a sample irradiated with measurement light having a predetermined wavelength, said apparatus comprising:
   a housing for defining a dark room; and
   a sample holder according to claim 18 disposed within said housing, said sample holder being located at a position where said sample holder is prevented from being irradiated with the measurement light.

29. An apparatus according to claim 28, further comprising an optical system disposed within said housing and placed in a light path through which the measurement light travels.

30. An apparatus according to claim 28, further comprising an optical monitor for monitoring a light intensity of the measurement light, said optical monitor being disposed within said housing and receiving a part of the measurement light.

31. An apparatus according to claim 28, further comprising a liquid amount adjusting system for constantly maintaining the liquid level of the liquid to be saved in the sample supporting section of said holder body.

32. An apparatus according to claim 31, wherein said liquid amount adjusting system comprises a liquid supplying mechanism for supplying the liquid into said sample supporting section of said holder body.

33. An apparatus according to claim 31, wherein said liquid amount adjusting system comprises a liquid recovering mechanism for removing a part of the liquid saved in said sample supporting section of said holder body, said liquid recovering mechanism including at least said liquid level adjusting mechanism and said liquid container.

34. An apparatus according to claim 28, further comprising a liquid temperature control system for controlling the temperature of the liquid to be saved into said sample supporting section of said holder body.

35. A sample holder applicable to an apparatus which measures an optical absorption of a sample with respect to measurement light having a predetermined wavelength by photoacoustic measurement, said sample holder comprising:
   a holder body having a sample supporting section which saves a predetermined amount of a liquid and supports the sample while a part of the sample is immersed in the liquid, said sample supporting section having an opening through which a part of the sample to be irradiated with the measurement light is placed above a liquid level of the liquid; and an acoustic sensor for detecting an acoustic signal generated upon a change in volume of the sample occurring due to the optical absorption of the sample irradiated with the measurement light, said acoustic sensor directly attached to said holder body by a adhesive, wherein said holder body is made of a material having a remarkably higher acoustic impedance than the liquid having an acoustic impedance within the range of $1.0 \times 10^6$ to $1.5 \times 10^6$ N.s.m$^{-3}$.

36. A sample holder according to claim 35, wherein said material of said holder body is one of aluminum and glass material.

* * * * *

UNITED STATES PATENT AND TRADEMARK OFFICE
CERTIFICATE OF CORRECTION

PATENT NO. : 5,673,114
DATED : September 30, 1997
INVENTOR(S) : Yoshijiro USHIO

It is certified that error appears in the above-identified patent and that said Letters Patent is hereby corrected as shown below:

On the title page, Item

-- [30] Foreign Application Priority Data

Jun. 27, 1995  [JP]  Japan ........7-160312

Nov. 7, 1995  [JP]  Japan ........7-288304 --

Signed and Sealed this

Twenty-fourth Day of March, 1998

Attest:

BRUCE LEHMAN

*Attesting Officer*    *Commissioner of Patents and Trademarks*